(12) United States Patent
Hess et al.

(10) Patent No.: US 10,314,565 B2
(45) Date of Patent: Jun. 11, 2019

(54) SURGICAL DEVICE HAVING ACTUATOR BIASING AND LOCKING FEATURES

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Jeffrey L. Savage, West Chester, OH (US); Adam D. Hensel, Cincinnati, OH (US); Nathan Daniel Grubbs, West Chester, OH (US)

(73) Assignee: ETHICON LLC, Guaynabo, PR (US)

( * ) Notice: Subject to any disclaimer, the term of this patent is extended or adjusted under 35 U.S.C. 154(b) by 818 days.

(21) Appl. No.: 14/836,069

(22) Filed: Aug. 26, 2015

(65) Prior Publication Data

US 2017/0055970 A1 Mar. 2, 2017

(51) Int. Cl.
*A61B 17/00* (2006.01)
*A61B 17/29* (2006.01)
*A61B 90/00* (2016.01)

(52) U.S. Cl.
CPC ........ *A61B 17/00234* (2013.01); *A61B 17/29* (2013.01); *A61B 17/2909* (2013.01);
(Continued)

(58) Field of Classification Search
CPC .......... A61B 17/00234; A61B 17/2909; A61B 17/29; A61B 2017/00371;
(Continued)

(56) References Cited

U.S. PATENT DOCUMENTS

| | | | |
|---|---|---|---|
| 3,043,309 | A | 7/1962 | McCarthy |
| 3,358,676 | A | 12/1967 | Frei et al. |

(Continued)

FOREIGN PATENT DOCUMENTS

| | | |
|---|---|---|
| DE | 101 49 421 A1 | 4/2003 |
| EP | 1 709 900 A1 | 10/2006 |

(Continued)

OTHER PUBLICATIONS

International Search Report dated Mar. 21, 2011; International Application No. PCT/US2010/051812 (7 pages).

(Continued)

*Primary Examiner* — Boniface N Nganga
(74) *Attorney, Agent, or Firm* — Mintz Levin Cohn Ferris Glovsky and Popeo, P.C.

(57) ABSTRACT

Surgical devices and methods are described. The surgical devices can generally include a housing having one or more actuators such as a closure actuator. An elongate shaft can extend distally from the housing and an end effector can be selectively coupled to a distal end of the shaft. The surgical device can include various features that prevent a user from actuating the device when the end effector is not properly coupled to the shaft. More specifically, the housing can include a locking member that can be pivoted or otherwise move relative the housing to cause various internal features of the housing to move to a ready-to-load position. With the locking member and actuator so positioned, an end effector can be loaded onto the shaft and the locking member can be moved from the ready-to-load position to the ready-to-actuate position, thus allowing the closure actuator to be in a ready-to-actuate position.

13 Claims, 14 Drawing Sheets

(52) U.S. Cl.
CPC ............ *A61B 2017/00371* (2013.01); *A61B 2017/00424* (2013.01); *A61B 2017/00876* (2013.01); *A61B 2017/2919* (2013.01); *A61B 2017/2925* (2013.01); *A61B 2017/2931* (2013.01); *A61B 2017/2946* (2013.01); *A61B 2090/0813* (2016.02)

(58) Field of Classification Search
CPC .. A61B 2017/00424; A61B 2017/2919; A61B 2017/2925; A61B 2017/2946; A61B 2017/2931; A61B 2017/00876; A61B 2090/0813
See application file for complete search history.

(56) References Cited

U.S. PATENT DOCUMENTS

| | | |
|---|---|---|
| 3,710,399 A | 1/1973 | Hurst |
| 3,893,448 A | 7/1975 | Brantigan |
| 3,906,217 A | 9/1975 | Lackore |
| 3,988,535 A | 10/1976 | Hickman et al. |
| 4,047,136 A | 9/1977 | Satto |
| 4,063,561 A | 12/1977 | McKenna |
| 4,099,192 A | 7/1978 | Aizawa et al. |
| 4,278,077 A | 7/1981 | Mizumoto |
| 4,384,584 A | 5/1983 | Chen |
| 4,585,282 A | 4/1986 | Bosley |
| 4,597,390 A | 7/1986 | Mulhollan et al. |
| 4,655,746 A | 4/1987 | Daniels et al. |
| 5,052,402 A | 10/1991 | Bencini et al. |
| 5,201,743 A | 4/1993 | Haber et al. |
| 5,282,806 A | 2/1994 | Haber et al. |
| 5,286,255 A | 2/1994 | Weber |
| 5,308,357 A | 5/1994 | Lichtman |
| 5,314,424 A | 5/1994 | Nicholas |
| 5,330,502 A | 7/1994 | Hassler et al. |
| 5,352,219 A | 10/1994 | Reddy |
| 5,392,917 A | 2/1995 | Alpern et al. |
| 5,417,203 A | 5/1995 | Tovey et al. |
| 5,441,059 A | 8/1995 | Dannan |
| 5,468,250 A | 11/1995 | Paraschac et al. |
| 5,502,698 A | 3/1996 | Mochizuki |
| 5,507,297 A | 4/1996 | Slater et al. |
| 5,540,648 A | 7/1996 | Yoon |
| 5,562,655 A | 10/1996 | Mittelstadt et al. |
| 5,578,052 A | 11/1996 | Koros et al. |
| 5,593,402 A | 1/1997 | Patrick |
| 5,613,937 A | 3/1997 | Garrison et al. |
| 5,618,303 A | 4/1997 | Marlow et al. |
| 5,716,326 A | 2/1998 | Dannan |
| 5,762,255 A | 6/1998 | Chrisman et al. |
| 5,792,165 A | 8/1998 | Klieman et al. |
| 5,810,877 A | 9/1998 | Roth et al. |
| 5,881,615 A | 3/1999 | Dahl et al. |
| 5,928,263 A | 7/1999 | Hoogeboom |
| 5,980,455 A | 11/1999 | Daniel et al. |
| 6,024,748 A | 2/2000 | Manzo et al. |
| 6,059,719 A | 5/2000 | Yamamoto et al. |
| 6,099,537 A | 8/2000 | Sugai et al. |
| 6,159,200 A | 12/2000 | Verdura et al. |
| 6,309,397 B1 | 10/2001 | Julian et al. |
| 6,315,789 B1 | 11/2001 | Cragg |
| 6,419,688 B1 | 7/2002 | Bacher et al. |
| 6,471,172 B1 | 10/2002 | Lemke et al. |
| 6,589,211 B1 | 7/2003 | MacLeod |
| 6,595,984 B1 | 7/2003 | DeGuillebon |
| 6,626,824 B2 | 9/2003 | Ruegg et al. |
| 6,635,071 B2 | 10/2003 | Boche et al. |
| 6,723,043 B2 | 4/2004 | Kleeman et al. |
| 6,770,081 B1 | 8/2004 | Cooper et al. |
| 6,776,165 B2 | 8/2004 | Jin |
| 6,827,712 B2 | 12/2004 | Tovey et al. |
| 6,860,878 B2 | 3/2005 | Brock |
| 6,869,395 B2 | 3/2005 | Page et al. |
| 6,884,213 B2 | 4/2005 | Raz et al. |
| 6,936,003 B2 | 8/2005 | Iddan |
| 6,942,674 B2 | 9/2005 | Belef et al. |
| 6,986,738 B2 | 1/2006 | Glukhovsky et al. |
| 6,994,708 B2 | 2/2006 | Manzo |
| 7,039,453 B2 | 5/2006 | Mullick et al. |
| 7,042,184 B2 | 5/2006 | Oleynikov et al. |
| 7,066,879 B2 | 6/2006 | Fowler et al. |
| 7,083,579 B2 | 8/2006 | Yokoi et al. |
| 7,122,028 B2 | 10/2006 | Looper et al. |
| 7,125,403 B2 | 10/2006 | Julian et al. |
| 7,169,104 B2 | 1/2007 | Ueda et al. |
| 7,199,545 B2 | 4/2007 | Oleynikov et al. |
| 7,211,094 B2 | 5/2007 | Gannoe et al. |
| 7,241,290 B2 | 7/2007 | Doyle et al. |
| 7,297,142 B2 | 11/2007 | Brock |
| 7,331,967 B2 | 2/2008 | Lee et al. |
| 7,429,259 B2 | 9/2008 | Cadeddu et al. |
| 7,448,993 B2 | 11/2008 | Yokoi et al. |
| 7,559,887 B2 | 7/2009 | Dannan |
| 7,566,331 B2 | 7/2009 | Looper et al. |
| 7,604,642 B2 | 10/2009 | Brock |
| 7,651,471 B2 | 1/2010 | Yokoi et al. |
| 7,666,181 B2 | 2/2010 | Abou El Kheir |
| 7,678,043 B2 | 3/2010 | Gilad |
| 7,691,103 B2 | 4/2010 | Fernandez et al. |
| 7,691,126 B2 | 4/2010 | Bacher |
| 7,699,835 B2 | 4/2010 | Lee et al. |
| 7,722,599 B2 | 5/2010 | Julian et al. |
| 7,862,553 B2 | 1/2011 | Ewaschuk |
| 7,894,882 B2 | 2/2011 | Mullick et al. |
| 7,901,398 B2 | 3/2011 | Stanczak et al. |
| 8,021,358 B2 | 9/2011 | Doyle et al. |
| 8,038,612 B2 | 10/2011 | Paz |
| 8,052,636 B2 | 11/2011 | Moll et al. |
| 8,057,502 B2 | 11/2011 | Maliglowka et al. |
| 8,088,062 B2 | 1/2012 | Zwolinski |
| 8,128,643 B2 | 3/2012 | Aranyi et al. |
| 8,182,414 B2 | 5/2012 | Handa et al. |
| 8,187,166 B2 | 5/2012 | Kuth et al. |
| 8,377,044 B2 | 2/2013 | Coe et al. |
| 8,397,335 B2 | 3/2013 | Gordin et al. |
| 8,398,544 B2 | 3/2013 | Altamirano |
| 8,409,076 B2 | 4/2013 | Pang et al. |
| 8,475,361 B2 | 7/2013 | Barlow et al. |
| 8,518,024 B2 | 8/2013 | Williams et al. |
| 8,623,011 B2 | 1/2014 | Spivey |
| 8,636,648 B2 | 1/2014 | Gazdzinski |
| 8,721,539 B2 | 5/2014 | Shohat et al. |
| 8,764,735 B2 | 7/2014 | Coe et al. |
| 8,764,769 B1 | 7/2014 | Rodriguez-Navarro et al. |
| 8,845,661 B2 | 9/2014 | D'Arcangelo et al. |
| 9,142,527 B2 | 9/2015 | Lee et al. |
| 9,282,879 B2 | 3/2016 | Farin et al. |
| 9,308,011 B2 | 4/2016 | Chao et al. |
| 9,408,628 B2 | 8/2016 | Altamirano |
| 9,451,937 B2 | 9/2016 | Parihar |
| 2001/0051766 A1 | 12/2001 | Gazdzinski |
| 2003/0060702 A1 | 3/2003 | Kuth et al. |
| 2003/0114731 A1 | 6/2003 | Cadeddu et al. |
| 2004/0093039 A1 | 5/2004 | Schumert |
| 2004/0133235 A1 | 7/2004 | Bacher |
| 2004/0152941 A1 | 8/2004 | Asmus et al. |
| 2005/0033354 A1 | 2/2005 | Montalvo et al. |
| 2005/0085697 A1 | 4/2005 | Yokoi et al. |
| 2005/0119640 A1 | 6/2005 | Sverduk et al. |
| 2005/0131396 A1 | 6/2005 | Stanczak et al. |
| 2005/0165449 A1 | 7/2005 | Cadeddu et al. |
| 2005/0215983 A1 | 9/2005 | Brock |
| 2005/0250984 A1 | 11/2005 | Lam et al. |
| 2005/0272972 A1 | 12/2005 | Iddan |
| 2005/0272974 A1 | 12/2005 | Iddan |
| 2005/0273139 A1 | 12/2005 | Krauss et al. |
| 2005/0288555 A1 | 12/2005 | Binmoeller |
| 2006/0079933 A1 | 4/2006 | Hushka et al. |
| 2006/0149135 A1 | 7/2006 | Paz |
| 2006/0184161 A1 | 8/2006 | Maahs et al. |
| 2006/0190035 A1 | 8/2006 | Hushka et al. |
| 2006/0195015 A1 | 8/2006 | Mullick et al. |
| 2006/0229592 A1 | 10/2006 | Yokoi et al. |

(56) References Cited

U.S. PATENT DOCUMENTS

| | | |
|---|---|---|
| 2006/0258905 A1 | 11/2006 | Kaji et al. |
| 2007/0010709 A1 | 1/2007 | Reinschke |
| 2007/0049966 A1 | 3/2007 | Bonadio et al. |
| 2007/0073247 A1 | 3/2007 | Ewaschuk |
| 2007/0093792 A1 | 4/2007 | Julian et al. |
| 2007/0123748 A1 | 5/2007 | Meglan |
| 2007/0156015 A1 | 7/2007 | Gilad |
| 2007/0255100 A1 | 11/2007 | Barlow et al. |
| 2007/0255273 A1 | 11/2007 | Fernandez et al. |
| 2007/0270651 A1 | 11/2007 | Gilad et al. |
| 2007/0299387 A1 | 12/2007 | Williams et al. |
| 2008/0004656 A1 | 1/2008 | Livneh |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 | 6/2008 | Schnell |
| 2008/0154299 A1 | 6/2008 | Livneh |
| 2008/0242939 A1 | 10/2008 | Johnston |
| 2008/0243106 A1 | 10/2008 | Coe et al. |
| 2008/0287926 A1 | 11/2008 | Abou El Kheir |
| 2008/0312499 A1 | 12/2008 | Handa et al. |
| 2009/0005636 A1 | 1/2009 | Pang et al. |
| 2009/0005638 A1 | 1/2009 | Zwolinski |
| 2009/0209947 A1 | 8/2009 | Gordin et al. |
| 2010/0249700 A1 | 9/2010 | Spivey |
| 2011/0040322 A1 | 2/2011 | Major |
| 2011/0087265 A1 | 4/2011 | Nobis et al. |
| 2011/0087266 A1 | 4/2011 | Conlon et al. |
| 2011/0087267 A1 | 4/2011 | Spivey et al. |
| 2011/0115891 A1 | 5/2011 | Trusty |
| 2011/0208007 A1 | 8/2011 | Shohat et al. |
| 2011/0230869 A1 | 9/2011 | Altamirano |
| 2011/0288560 A1 | 11/2011 | Shohat et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1 | 3/2012 | Nobis et al. |
| 2012/0083826 A1 | 4/2012 | Chao et al. |
| 2012/0088965 A1 | 4/2012 | Stokes et al. |
| 2012/0089093 A1 | 4/2012 | Trusty |
| 2012/0095298 A1 | 4/2012 | Stefanchik et al. |
| 2012/0259325 A1* | 10/2012 | Houser .................. A61B 17/29 606/33 |
| 2012/0316575 A1 | 12/2012 | Farin et al. |
| 2013/0138091 A1 | 5/2013 | Coe et al. |
| 2013/0138092 A1* | 5/2013 | Hinchliffe .......... A61B 17/1608 606/1 |
| 2014/0005474 A1 | 1/2014 | Farin et al. |
| 2014/0066711 A1 | 3/2014 | Farin et al. |
| 2014/0088569 A1 | 3/2014 | Parihar et al. |
| 2014/0088637 A1 | 3/2014 | Parihar et al. |
| 2014/0088638 A1 | 3/2014 | Parihar |
| 2014/0243799 A1 | 8/2014 | Parihar |
| 2014/0243800 A1 | 8/2014 | Parihar |
| 2014/0276666 A1* | 9/2014 | Malkowski ............ A61B 17/29 606/1 |
| 2014/0277018 A1 | 9/2014 | Parihar |
| 2014/0378953 A1 | 12/2014 | Coe et al. |
| 2015/0088191 A1 | 3/2015 | Coe et al. |

FOREIGN PATENT DOCUMENTS

| | | | |
|---|---|---|---|
| JP | 2005-261734 A | 9/2005 | |
| JP | 2008-518716 A | 6/2008 | |
| WO | 2008/015666 A2 | 2/2008 | |
| WO | 2010/060436 A1 | 6/2010 | |
| WO | 2010/081482 A1 | 7/2010 | |
| WO | 2010/111319 A1 | 9/2010 | |
| WO | 2010/114634 A1 | 10/2010 | |
| WO | 2011/044353 A1 | 4/2011 | |
| WO | 2011/089565 A1 | 7/2011 | |
| WO | 2012/035524 A2 | 3/2012 | |
| WO | 2012/040183 A1 | 3/2012 | |
| WO | 2012/112622 A2 | 8/2012 | |
| WO | WO 2012112622 A2 * | 8/2012 | ............. A61B 17/29 |
| WO | 2012/126967 A2 | 9/2012 | |
| WO | 2013/007764 A2 | 1/2013 | |
| WO | 2013/048963 A2 | 4/2013 | |
| WO | 2014/052177 A1 | 4/2014 | |
| WO | 2014145595 A2 | 9/2014 | |

OTHER PUBLICATIONS

International Preliminary Report dated Apr. 19, 2012; International Application No. PCT/US2010/051812 (10 pages).
International Search Report dated Mar. 2, 2012; International Application No. PCT/US2011/050198 (7 pages).
International Preliminary Report dated Mar. 14, 2013; International Application No. PCT/US2011/050198 (10 pages).
International Search Report dated Dec. 12, 2011; International Application No. PCT/US2011/052327 (5 pages).
International Preliminary Report dated Apr. 4, 2013; International Application No. PCT/US2011/052327 (9 pages).
International Search Report dated Apr. 3, 2013; International Application No. PCT/US2012/056900 (3 pages).
International Preliminary Report dated Apr. 10, 2014; International Application No. PCT/US2012/056900 (8 pages).
International Search Report dated Dec. 20, 2013; International Application No. PCT/US2013/060803 (3 pages).
International Preliminary Report dated Apr. 9, 2015; International Application No. PCT/US2013/060803 (9 pages).
International Search Report dated May 28, 2014; International Application No. PCT/US2014/015738 (4 pages).
International Preliminary Report on Patentability dated Sep. 11, 2015; International Application No. PCT/US2014/015738 (12 pages).
US Application as filed on Oct. 9, 2009 for U.S. Appl. No. 12/576,529 (18 pages).
Extended European Search Report for European Application No. 16185870.9, dated Jan. 11, 2017 (7 pages).
International Search Report for International Application No. PCT/US2016/046550, dated Nov. 16, 2016 (8 pages).

* cited by examiner

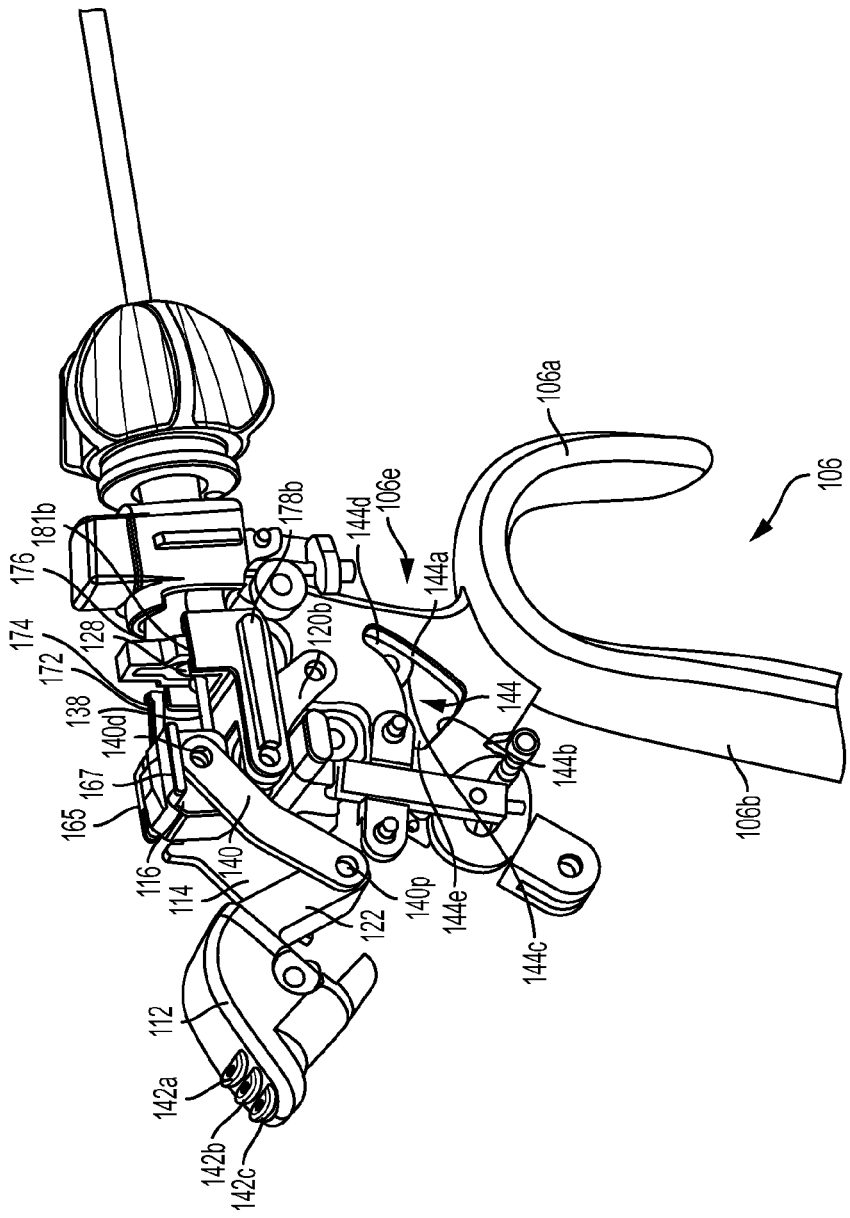

SURGICAL DEVICE HAVING ACTUATOR BIASING AND LOCKING FEATURES

FIELD

The present application relates to surgical devices having actuator biasing and locking features.

BACKGROUND

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic, arthroscopic, natural orifice intraluminal, and natural orifice transluminal procedures.

Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to manipulate the patient's internal tissue while maintaining pneumoperitoneum. For example, trocars are often used to provide a port through which endoscopic surgical instruments are passed. Trocars generally have an instrument seal which prevents the insufflatory fluid from escaping while an instrument is positioned in the trocar.

Various surgical instruments can be configured to manipulate tissue during an endoscopic surgical procedure. Some surgical instruments can have a housing or handle portion, an elongate shaft, and an end effector that can be selectively coupled to the shaft and can articulate relative to the shaft. In certain aspects, the device can include one or more modular features, such as having a modular end effector that can be selectively attached to and detached from the shaft. While the modularity of the end effector can improve the device's versatility, the modularity may cause a user to actuate the device improperly. For example, a user may attempt to actuate jaws of the end effector when the end effector is not properly coupled to the shaft such as when the jaws are improperly aligned or if one or more mating features between the end effector and the shaft fail. This can delay the procedure and a user may erroneously believe that the device is damaged and unusable when instead there is an improperly loaded end effector. Still further, during loading of an end effector a closure actuator has to be at a particular angle relative to the device's housing to ensure that the device's components are in the proper position to receive the end effector. Some prior art devices include an external kickstand or latch pivotally connected to a housing such that the latch moves between a locked position and an unlocked position. When the latch is in a locked position, the latch engages a closure actuator to hold the actuator at a particular angle relative to the housing. However, a user may forget to engage the latch prior to beginning loading the end effector onto the shaft and this can lead to an improperly loaded end effector and/or can delay the procedure. It can also be difficult to operate the latch while holding the device and performing other steps of a surgical procedure.

Accordingly, there is a need for endoscopic surgical methods and devices having alternative actuator biasing and locking features.

SUMMARY

Surgical devices having actuator biasing and locking features are provided to facilitate loading an end effector onto a surgical device. In one exemplary embodiment, a surgical device includes a housing, a closure actuator coupled to the housing and configured to pivot with respect to the housing, an elongate shaft extending distally from the housing, and a locking member operably coupled to one or more actuation components disposed within the housing. The one or more actuation components can be coupled to the closure actuator such that movement of the locking member effects movement of the closure actuator. The elongate shaft can have a loading zone located at a distal end of the elongate shaft, the loading zone being configured to receive an end effector. The locking member can be configured to move to a load position in which the closure actuator is held at a fixed location with respect to the housing such that an end effector can be loaded onto the distal end of the elongate shaft at the loading zone.

The device can vary in any number of ways. For example, the device can include an inner shaft disposed within an inner lumen of the elongate shaft, the inner shaft having a proximal end coupled to the one or more actuation components disposed within the housing, the inner shaft being configured to translate relative to the elongate shaft along a longitudinal axis thereof, and the inner shaft being configured to lock an end effector to the distal end of the elongate shaft at the loading zone when a distal end of the inner shaft is disposed within a portion of the inner lumen contained within the loading zone. When the locking member is in the load position, the distal end of the inner shaft can be located proximal of the loading zone. The device can include an intermediate shaft disposed between the elongate shaft and the inner shaft. The intermediate shaft can have an advanced position in which a portion of the intermediate shaft that extends distally beyond the distal end of the elongate shaft is part of the loading zone. The locking member can also have a use position at which the closure actuator is located further from the housing than when the locking member is in the load position. The closure actuator can include an opening formed in a portion thereof, with at least a portion of the opening being disposed within the housing, and a cam surface that is configured to move the closure actuator towards the fixed location in response to the locking member moving to the load position.

The one or more actuation components can also vary. For example, the one or more actuation components can include a plate pivotally coupled to the closure actuator and configured to be slidably coupled to the inner shaft. The one or more actuation components can further include a sled and a linkage, the sled being coupled to the proximal end of the inner shaft and being configured to slide along a path within the housing, the sled engaging the plate when the sled is positioned on a proximal portion of the path and a linkage having a first end coupled to the locking member and a second end coupled to the sled.

In some embodiments, a surgical device includes a housing, a closure actuator coupled to the housing at a distal, lower portion of the housing, the closure actuator being configured to pivot with respect to the housing, an elongate shaft extending distally from a distal, upper portion of the housing, the elongate shaft having a distal end configured to receive an end effector, and a locking member extending from a proximal, upper portion of the housing. The locking member can be configured to move between a loading position at which an end effector can be loaded onto the distal end of the elongate shaft, and a firing position at which the closure actuator can be operated to control an end effector loaded onto the distal end of the elongate shaft.

The device can vary in any number of ways. For example, the locking member can be configured to pivot with respect to the housing between the loading position and the firing position. For another example, the housing can include a handle portion configured to be gripped by a hand of an operator, the locking member being configured to be controlled by one or more fingers or thumb of the hand of the operator while the hand remains gripping the handle portion.

The device can have one or more shafts. For example, an inner shaft can be disposed within an inner lumen of the elongate shaft and can be configured to translate relative to the elongate shaft along a longitudinal axis thereof, the inner shaft further being configured to lock an end effector to the distal end of the elongate shaft when a distal end of the inner shaft is disposed within a portion of the inner lumen that has an end effector disposed therearound. When the locking member is in the loading position, the distal end of the inner shaft can be located proximal of the portion of the inner lumen that has an end effector disposed therearound, and when the locking member is in the firing position, the distal end of the inner shaft can be located within the portion of the inner lumen that has an end effector disposed therearound. The device can further include an intermediate shaft disposed between the elongate shaft and the inner shaft. The intermediate shaft can have an advanced position in which a portion of the intermediate shaft that extends distally beyond the distal end of the elongate shaft is configured to receive an end effector.

The housing can include various other components. A plate can be disposed within the housing and pivotally coupled to the closure actuator and configured to be slidably coupled to the inner shaft. A sled can be configured to travel along a path within the housing and can couple to a proximal end of the inner shaft, the sled engaging the plate when the sled travels along a portion of the path. The housing can further include a linkage having a first end coupled to the locking member and a second end coupled to the sled. In some embodiments, a pin can be disposed on the sled and can be configured to engage the plate to prevent the plate and the closure actuator from advancing distally when the locking member is in the loading position.

An exemplary surgical method includes moving a locking member of a surgical device to a loading position, which also causes a closure actuator of the surgical device to move to a fixed loading position. When the locking member is in the loading position and the closure actuator is in the fixed loading position, an end effector can be loaded onto a surgical end of the surgical device. The method can further include coupling an end effector to the surgical end of the surgical device.

In some embodiments, coupling an end effector to the surgical end of the surgical device can include distally advancing an inner shaft of the surgical device within a lumen of an outer shaft of the surgical device. In certain aspects, distally advancing the inner shaft of the surgical device within the lumen of the outer shaft of the surgical device can expand one or more arms of an intermediate shaft disposed between the outer shaft and the inner shaft radially outward to couple the end effector to the surgical end of the surgical device.

The surgical method can vary in any number of ways, and can include forming an incision in tissue using a distal end of the inner shaft prior to moving a locking member of a surgical device to the loading position. In some embodiments, the surgical end of the surgical device can be inserted to a surgical site through a first incision and a loader can be inserted to a surgical site through a second incision, the loader being configured to present an end effector to the surgical end of the surgical device.

BRIEF DESCRIPTION OF DRAWINGS

This disclosure will be more fully understood from the following detailed description taken in conjunction with the accompanying drawings, in which:

FIG. 5A is a perspective view of actuation components of the housing of FIG. 1B viewed from one side of the device;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, to the extent features, sides, or steps are described as being "first" or "second," such numerical ordering is generally arbitrary, and thus such numbering can be interchangeable.

Surgical devices are described and can generally include a housing or handle portion having one or more actuators, such as a closure actuator, that operates an end effector. An elongate shaft can extend from the housing and a distal end of the shaft can be configured to selectively couple to an end effector in vivo or ex vivo. The device can include various features that prevent a user from actuating the device when the end effector is not properly coupled to the shaft. More specifically, the housing can include a locking member that can be pivoted or otherwise moved relative the housing to cause various internal actuation components of the housing to move to a ready-to-load position (also referred to as a loading position). When the components of the device are in the ready-to-load position, an end effector can be loaded onto the distal end of the shaft. When the end effector is loaded onto the shaft, the locking member and the closure actuator can be moved to a ready-to-actuate position (also referred to as a firing position) in which a user can engage the closure actuator to operate the end effector. Conveniently, the locking member can be operated with one or more fingers or thumb while a user can still grasp the housing with a single hand to move the locking member and the actuation components between the ready-to-load and ready-to-actuate positions.

Figure 1A:
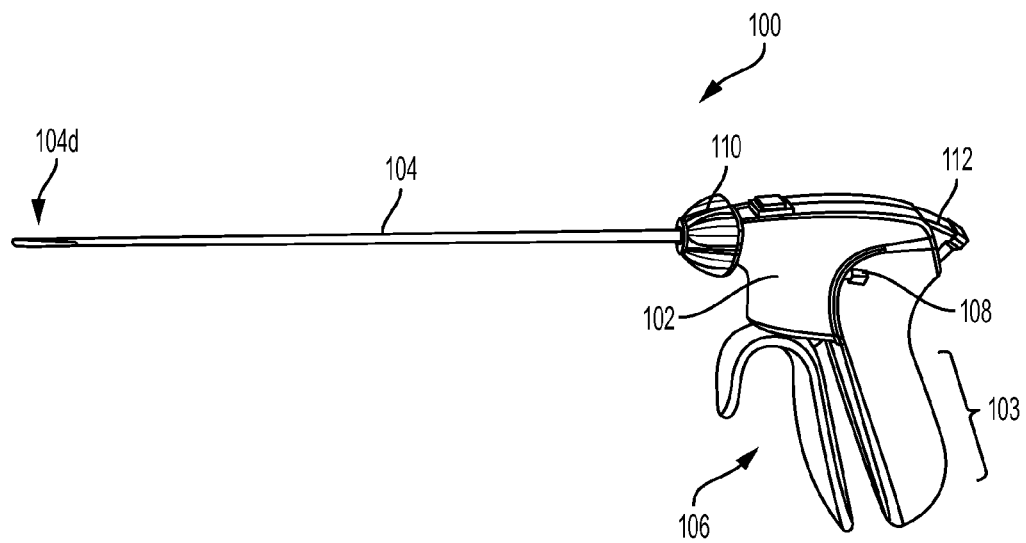
FIG. 1A is a side view of a modular surgical device having an elongate shaft with a distal mating feature that can couple to an end effector.

FIG. 1A shows an exemplary instrument or device 100 having a housing or handle portion 102 and an outer elongate shaft 104 extending distally from the housing 102, the shaft 104 being configured to have an end effector (not shown) selectively coupled to it. As shown, the elongate shaft 104 can extend from a distal, upper portion of the housing 102, and it can be removably and replaceably attached to operable components in the housing 102 as illustrated herein and as otherwise known to those skilled in the art. The housing 102 can include a stationary arm 103 and a closure actuator 106, such as a pivotable trigger, that is configured to move relative to the housing 102 to actuate an end effector when an end effector is coupled to the shaft 104. As shown, the closure actuator 106 can be coupled to a distal, lower portion of the housing 102.

The device 100 can include various components that facilitate use of the device during a surgical procedure. For example, the housing 102 can include a locking switch 108 that can be selectively activated to lock the closure actuator 106 in a fixed angular position relative to the housing 102, such as via ratcheting features that will hold the closure actuator 106 in the position even when a manual force is not applied by a user. By way of further example, the housing 102 can include a knob 110 configured to rotate the elongate shaft 104, and thus an end effector coupled thereto. The knob 110 can include one or more features that can lock out the knob 110 in proportion to the force applied to the closure actuator 106 to move it towards the housing 102 and/or the rotational capability of the knob can be reduced by friction as a load is generated through the end effector. This can help prevent inadvertent rotation of the knob 110 and of the end effector when the closure actuator 106 is engaged and the end effector is being actuated. Still further, the device 100 can include both intermediate and inner shafts 128 and 138, respectively, (shown in FIG. 2B) disposed within the elongate shaft 104 and being configured to move proximally and distally relative to the elongate shaft 104. As will be described in greater detail below, both the intermediate and inner shafts 128, 138 can be used to assist in mating end effectors to the elongate shaft. Further, the intermediate shaft 128 can be used to actuate such end effectors, and a distal end of the inner shaft 138 can include a pointed obturator tip that can be used to pierce through tissue. Additionally, the device 100 can have a locking member 112 disposed along a proximal, upper portion of the housing 102 and the locking member 112 can cooperate with actuation components disposed in the housing 102 to place the device in both the ready-to-load and ready-to-actuate positions.

Figure 1B:
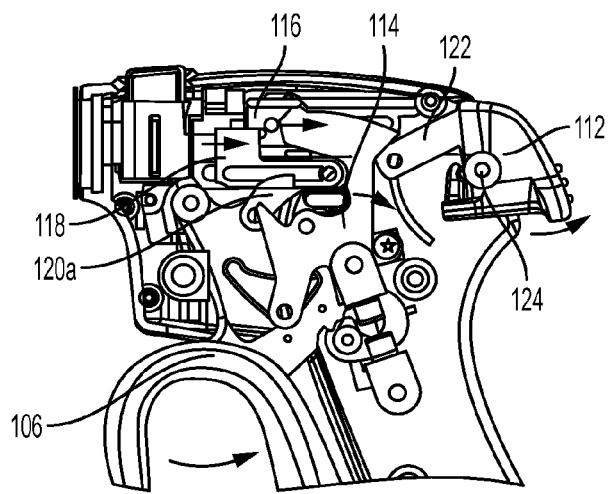
FIG. 1B is a side, semi-transparent view of a housing of the surgical device of FIG. 1A.

FIG. 1B shows various components internal to the housing 102 that can cooperate with the locking member 112 to hold the closure actuator 106 in a ready-to-load position and to retract the inner shaft along a longitudinal axis L of the shaft 104, relative to the shaft 104, in preparation for loading an end effector onto the shaft 104. As shown, the housing 102 can further include a pivotable plate member 114, an inner shaft sled 116, and an intermediate shaft sled 118. A first linkage 120a can couple the plate member 114 to the intermediate shaft sled 118. Additionally, a second linkage 140 (shown in FIG. 5A) can couple an internal arm 122 of the locking member 112 to the inner shaft sled 116 such that when the locking member 112 is pivoted in a counter clockwise direction about its pivot point 124, the inner shaft sled 116 moves proximally within the housing. As will be described in greater detail below, these connections between the components can ensure that the inner and intermediate shafts coupled to the sleds 116, 118 and the closure actuator 106 are in the proper position for loading an end effector onto the distal end 104d of the shaft 104.

Figure 2A:
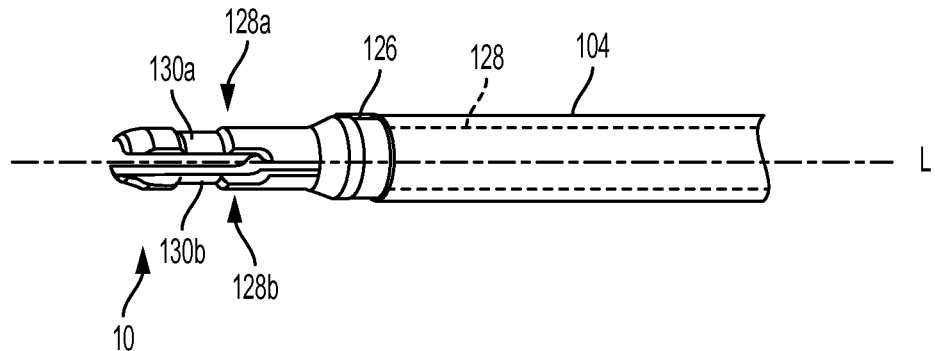
FIG. 2A is a side view of the distal mating feature of the elongate shaft of FIG. 1A.
Figure 2B:
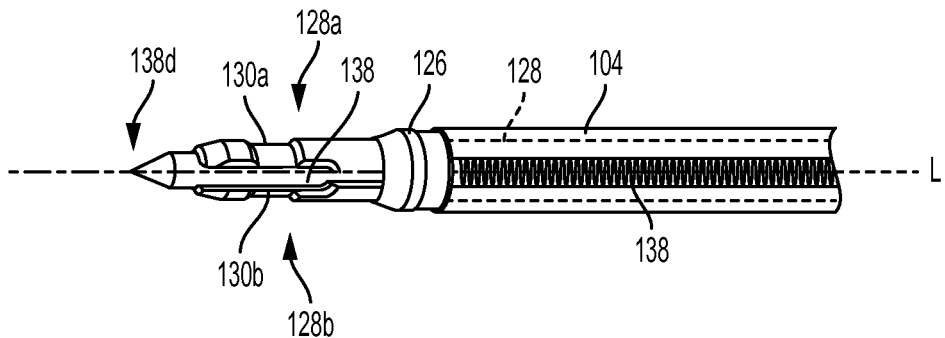
FIG. 2B is a side view of the distal mating feature of FIG. 2A having an obturator extending distally therethrough.

FIGS. 2A and 2B illustrate the distal end 104d of the shaft 104 in greater detail, including exemplary attachment mechanisms located at the distal end 104d of the elongate shaft 104 so that an end effector (not shown in FIGS. 2A and 2B) can be mated to the shaft 104. The attachment mechanisms can form a loading zone 10 for loading an end effector. While the attachment mechanism can vary, in the illustrated embodiment a circumferential groove 126 can be positioned around an outer surface of a distal portion of the shaft 104. First and second arms 128a, 128b can project distally from the distal end 104d of the shaft 104 and can be coupled to or otherwise integrally formed on an intermediate shaft 128. The arms 128a, 128b can be axially slidable relative the elongate shaft 104, for instance to actuate an end effector coupled to the elongate shaft 104, and can be resiliently deflectable medially into the gap. The arms 128a, 128b can each have a mating feature, which in this embodiment is a stepped lateral notch 130a, 130b.

A distal tip 138d of an inner shaft 138 (shown as a shaded region in FIG. 2B) can be positioned medially relative to the arms 128a, 128b and can be axially slidable relative to the arms 128a, 128b. More specifically, the distal tip 138d of the inner shaft 138 can slide between an unlocked position in which the distal tip 138d of the inner shaft 138 is proximal to the arms 128a, 128b, i.e., proximal of the loading zone 10, allowing medial deflection of the arms 128a, 128b (as shown in FIG. 2A), and a locked position in which the distal tip 138d of the inner shaft 138 is aligned with or distal to the arms 128a, 128b, i.e., aligned with or distal of the loading zone 10, and to prevent medial deflection of the arms 128a, 128b (as shown in FIG. 2B). In certain aspects, the inner shaft 138 and the arms 128a, 128b can slide independently along the longitudinal axis L of the elongate shaft 104. As shown in the embodiment of FIG. 2B, the distal tip 138d of the inner shaft 138 is also referred to herein as an obturator tip which can be pointed and/or sharpened such that the distal tip 138d can pierce through tissue. In the illustrated embodiment, the distal ends of the arms 128a, 128b and the distal end 104d of the elongate shaft 104 can taper from a proximal-to-distal direction and this can facilitate passing the arms 128a, 138b and the elongate shaft 104 through an incision (not shown), such as an incision formed by the distal tip 138d. As will be appreciated by persons skilled in the art, the distal tip 138d of the inner shaft 138 need not be sharpened or pointed and the outer and intermediate shafts can include various types of attachment mechanisms for mating with an end effector and need not include a taper, grooves, etc.

Figure 3A:
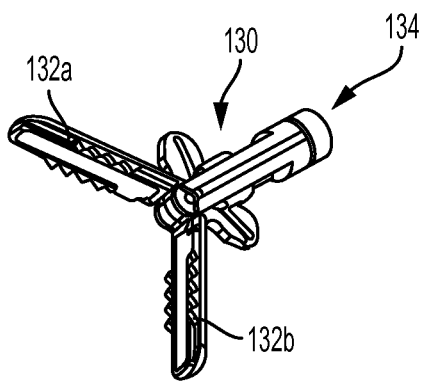
FIGS. 3A-3D are perspective views of various end effectors that can be coupled to the elongate shaft of the surgical device of FIG. 1A.
Figure 3B:
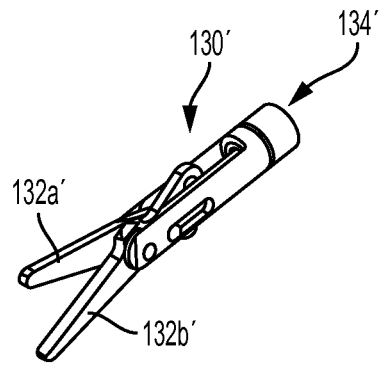
Figure 3C:
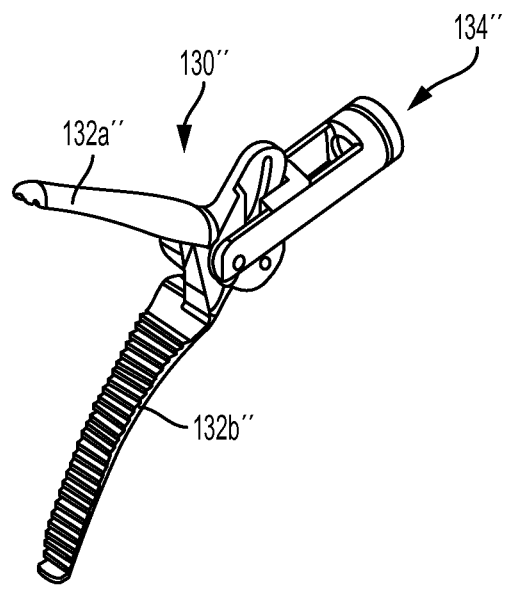
Figure 3D:
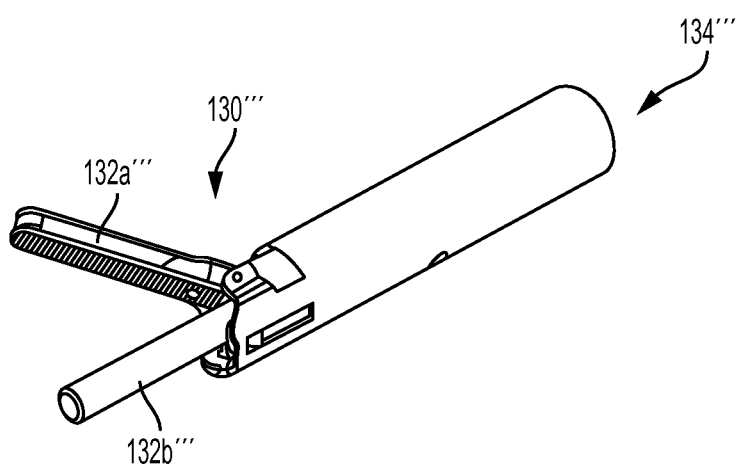

FIGS. 3A-3D provide non-limiting examples of end effectors that can be attached to the instrument 100. All or some of the end effectors can be provided in a kit so a surgeon can interchange the end effectors as needed for a particular surgical procedure. FIG. 3A illustrates a bi-polar jawed end effector 130 having first and second jaws 132a, 132b, FIG. 3B illustrates a cutting shears end effector 130' having first and second jaws 132a', 132b', FIG. 3C illustrates a Maryland dissector end 130" effector having first and second jaws 132a", 132b", and FIG. 3D illustrates an ultrasonic shears end effector 130''' having first and second jaws 132a''', 132b'''. Each of the end effectors 130, 130', 130", and 130''' can have a proximal opening formed 134, 134', 134", 134''' therein that can be configured to mate with attachment mechanisms or features of or otherwise associated with the intermediate shaft 128 and the outer shaft 104. For example, in some embodiments the openings 134, 134', 134", and 134''' can be sized and shaped to extend over the first and second arms 128a, 128b of FIGS. 2A and 2B. While the illustrated end effectors 130, 130', 130", and 130''' have cooperating jaws, the end effectors 130, 130', 130", and 130''' need not include jaws and/or the effectors could also include hook knives, snares, and the like. As will be appreciated, any of the end effectors 130, 130', 130", and 130''' can also be configured to transmit energy to tissue and in these embodiments the housing and the shaft of the surgical instrument can have appropriate energy transmission mechanisms. For example, appropriate electrical connections can be added to the bi-polar jawed end effector 130' of FIG. 3A and can extend through the elongate shaft 104. Similarly, an ultrasonic transducer and waveguide can be added to the ultrasonic shears end effector 130''' of FIG. 3D.

Figure 3E:
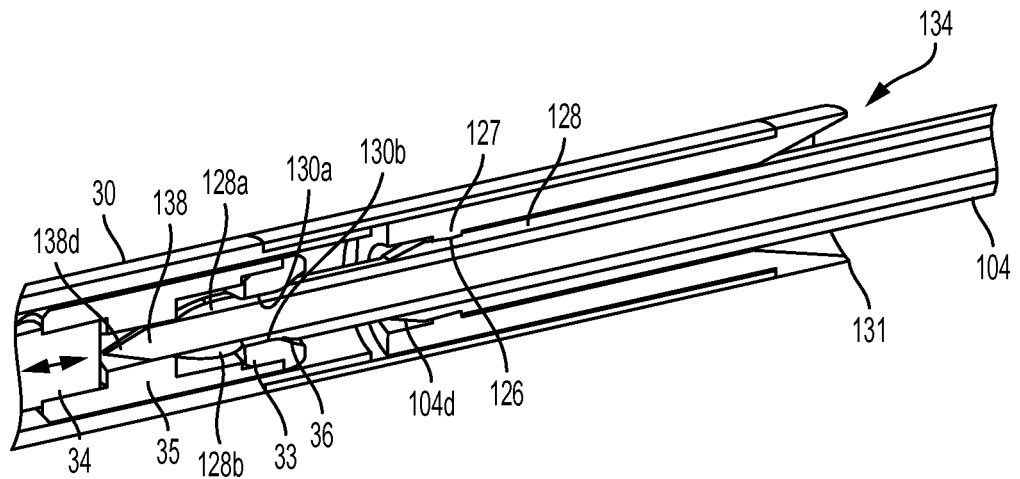
FIG. 3E is a perspective, cross-sectional view of a distal end of the elongate shaft of the device of FIG. 1A coupled to an end effector.
Figure 3F:
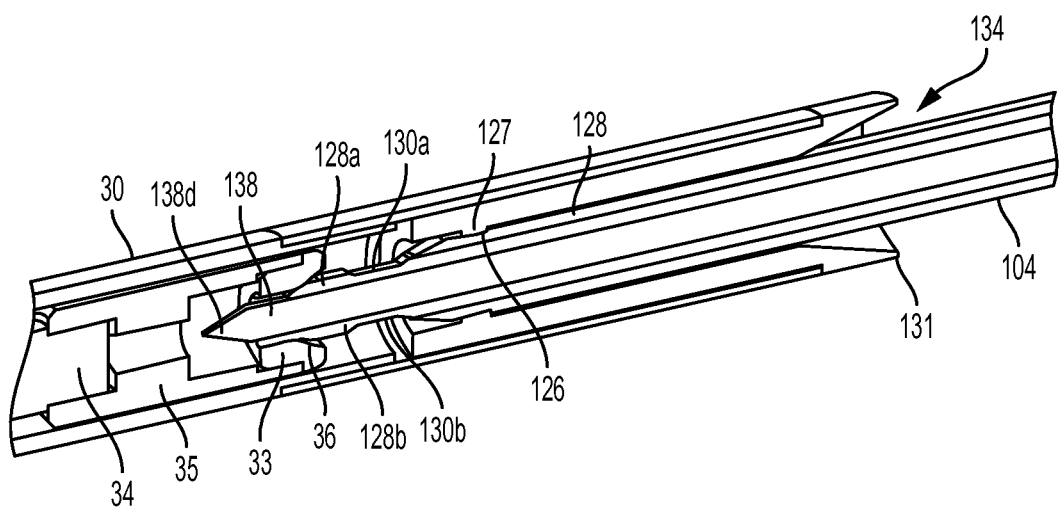
FIG. 3F is a perspective, cross-sectional view of the distal end of the elongate shaft and end effector of FIG. 3E with the end effector in a pushed-off configuration.

End effectors such as those illustrated in FIGS. 3A-3D can be mated to the elongate shaft 104 in a variety of ways. FIG. 3E illustrates an exemplary interaction between an end effector 30 and the intermediate and inner shafts 128, 138. As shown, the end effector 30 has a proximal end 31 that extends over a distal end 104d of the elongate shaft 104. In the illustrated embodiment, the groove 126 of the arms 128a, 128b of the intermediate shaft 128 mates with a rib 27 of the end effector 30 preventing relative axial motion. The lateral grooves 130a, 130b of the arms 128a, 128b mate to a ring 33 of the end effector 30 preventing relative axial motion. Rib 32 is rigidly connected to the outer housing 37 of the end effector 30, and the ring 33 is rigidly and fixedly connected to a jaw actuator 34 of the end effector 30 via the coupling 35. Accordingly, axial movement of the arms 128a, 128b relative the intermediate shaft 128 can cause axial movement of the jaw actuator 34 relative the housing 37 of the end effector 30, thereby causing jaws (not shown) of the end effector 30 to open and close. FIG. 3F illustrates the end effector 30 ready to be detached from the elongate shaft 104. In particular, distally advancing the arms 128a, 128b of the intermediate shaft can push the ring 33 distally until the rib 27 unseats from the groove 126 and allows the distal end 104d of the elongate shaft 104 to be removed from the end effector 30.

Figure 4:
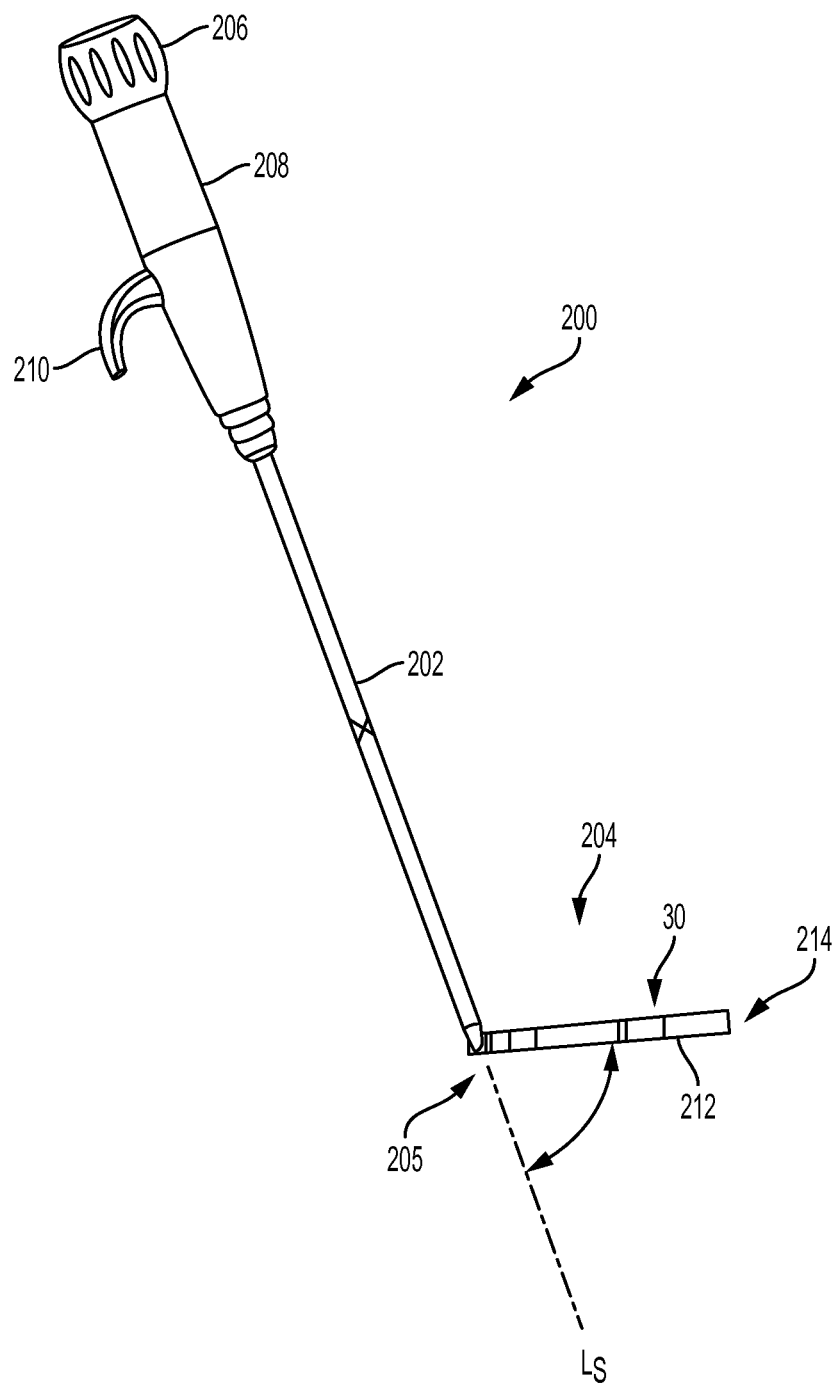
FIG. 4 is a perspective view of a loader device that can be used to load an end effector onto the surgical device of FIG. 1A.

An exemplary loading device 200 is shown in FIG. 4. The loader 200 can have a rigid and substantially straight shaft 202 as shown, or the shaft 202 can be curved and/or flexible, which would be beneficial for introducing the shaft 202 into a natural orifice. The loader 200 can have an articulating distal portion or tube 204 controlled by one or more actuators, such as a rotatable knob 206 disposed on a handle 208 of the loader 200, and the distal portion 204 can be articulated prior to or after it is inserted into a surgical site. A pivot joint 205 can couple the tube 204 to the shaft 202 and the tube 204 can be angulated relative to the shaft 202, as shown, by activating the actuator 206. An arm 210 can be connected to and extend from an outer surface of the handle 208 to facilitate a user grasping the handle 208 and rotational orientation of the articulated distal portion 204 about a longitudinal axis $L_S$ of the shaft 202. The loader 200 can be configured to hold an end effector therein and load the end effector onto the shaft 104 of the instrument 100. In the illustrated embodiment, the distal portion 204 of the loader 200 includes a tube 212 of an end effector 30, the tube 212 having an opening 214. While the end effector 30 is shown, any end effector can be used including the end effectors previously described. The distal portion 204 can include one or more engagement features (not shown) for holding the end effector 30 therein. While the engagement feature may vary, in an exemplary embodiment a plurality of leaf springs (not shown) can be disposed within the distal portion 204 and can provide an interference fit with an end effector to frictionally hold the end effector 30 in the distal portion 204 of the loader 200. In the illustrated embodiment, when the end effector is loaded in the distal portion 204, a distal end of the end effector 30 is positioned therein. This arrangement prevents the jaws (not shown) of the end effector 30 from opening when the end effector 30 is positioned within the distal portion 204 of the loader 200.

In another embodiment (not shown), a loader can have a distal portion that is selectively attachable and detachable to the shaft. This can be accomplished in various ways such as using a bayonet connection, but other connections are also contemplated including snap connections, threaded connections, and the like. One advantage of this embodiment is that a single sized tube may not accommodate certain end effectors and the ability to select the appropriate type of feature for holding an end effector increases the versatility of the loader.

Figure 5B:
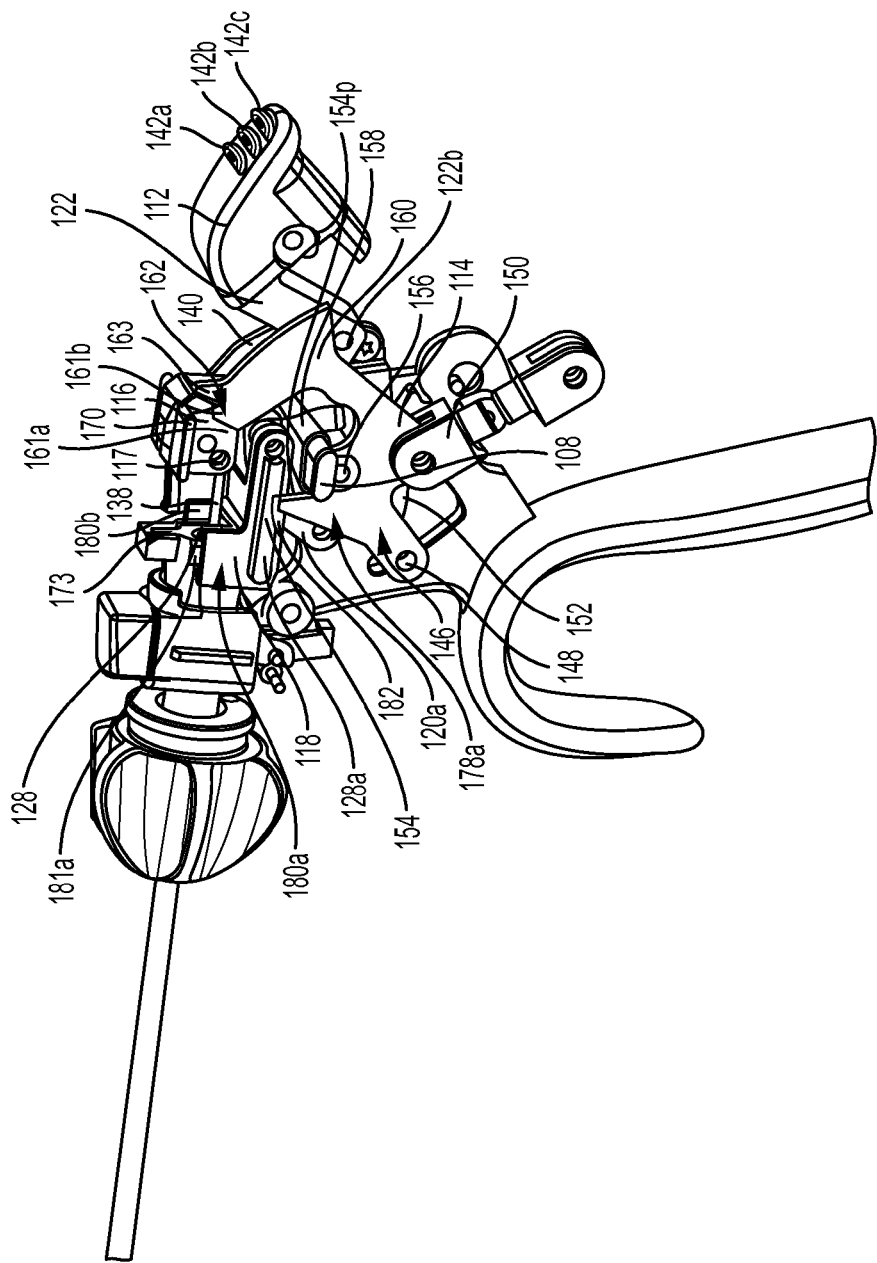
FIG. 5B is a perspective view of the actuation components of FIG. 5A viewed from a second side of the device.
Figure 7A:
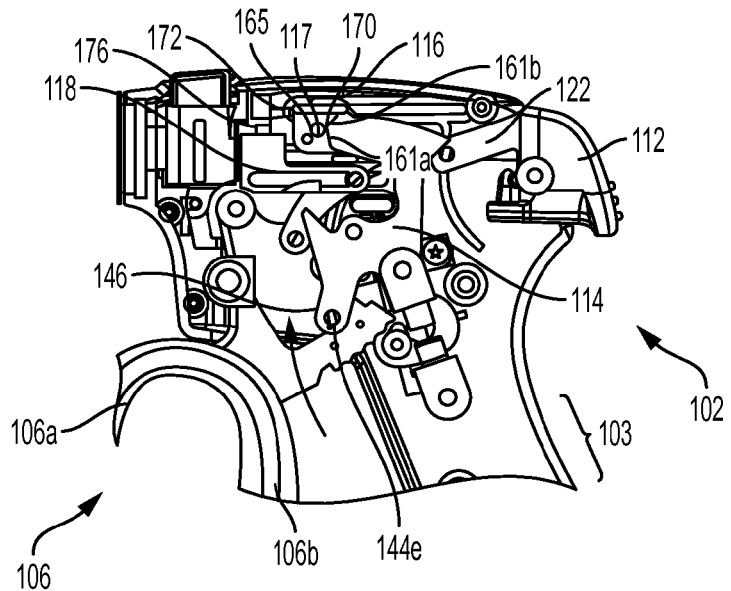
FIG. 7A is a side, semi-transparent view of the housing of the surgical device of FIG. 1A in a first position in which an end effector is not attached to the device and a locking member is in a first position.

FIGS. 5A and 5B illustrate internal actuation components disposed in the housing (which is hidden in this view). Referring first to the locking member 112, one or more features that increase friction between a user's finger and/or thumb such as grooves or projections can be formed on the locking member 112. In the illustrated embodiment, the locking member 112 has three crescent-shaped protrusions 142a, 142b, 142c spaced along an upper surface of the locking member 112. The arm 122 of the locking member 112 can have a terminal end 122b that couples to a proximal end 140p of a second linkage 140, the second linkage 140 having a distal end that couples to an outer surface of the inner shaft sled 116. The closure actuator 106 can include a first arm portion 106a and a second arm portion 106b positioned outside of the housing, as shown in FIG. 7A, and can define a substantially U-shaped recess disposed therebetween such that a user can position his/her fingers and/or palm between the arm portions 106a, 106b.

The closure actuator 106 can further include an extension plate 106e disposed substantially inside of the housing and configured to interact with one or more of the actuation components. The extension plate 106e can be coupled to or otherwise integrally formed on an upper surface defined by the first and second arm portions 106a, 106b. The extension plate 106e can be shaped in various ways, but in the illustrated embodiment has a substantially triangular cross-sectional shape and a relatively narrow width that is less than a width of the closure actuator 106. The extension plate 106e can have an opening 144 formed herein that can act as a cam and guide movement of one or more of the actuation components. The opening 144 can be shaped in various ways, but in the illustrated embodiment has a substantially triangular cross-sectional shape defined by first and second planar sides 144a, 144b, a third curved side 144c, and first and second rounded ends 144d, 144e where the first and second planar sides 144a, 144b meet with the third curved side 144c. A proximal surface of the extension plate 106e can optionally include one or more features that can allow incremental advancement of the closure actuator 106 toward and away from the housing, such as ratchet teeth 109 shown in FIG. 5C. An upper side of the extension plate 106e can have a plurality of curves, planar sides, etc. that can provide space for the other actuation components disposed in the housing. The closure actuator 106 and the extension plate 106e, and the interaction with the other actuation components provided herein, can result in improved actuation of the closure actuator 106 and can reduce slop and dead actuator travel.

Figure 5C:
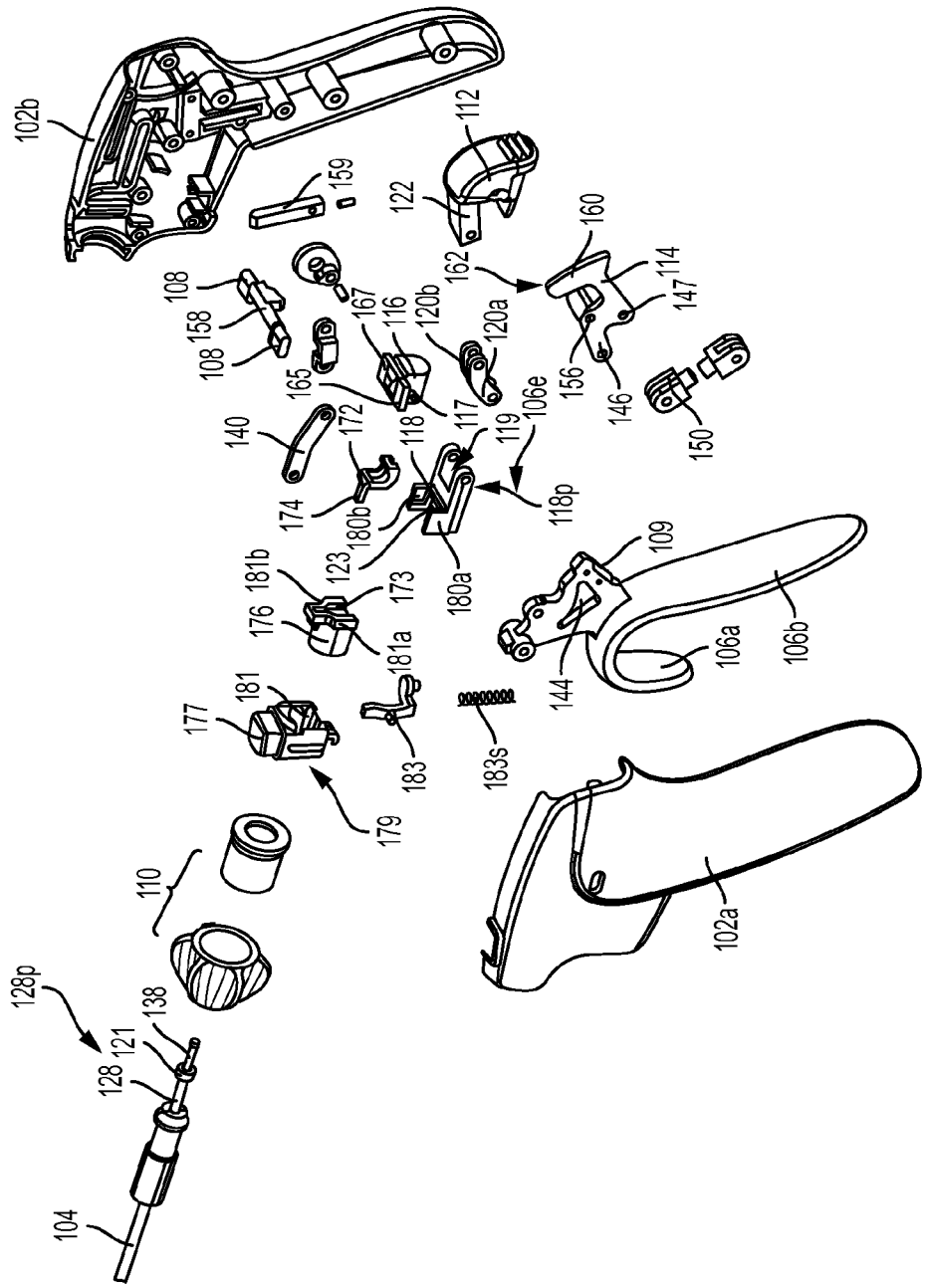
FIG. 5C is an exploded view of the actuation components of FIGS. 5A and 5B.

As previously mentioned, the pivotable plate member 114 can pivot within the housing and is shown in greater detail in FIGS. 5B and 5C. The plate member 114 can be shaped in various ways and can include one or more curved or planar surfaces that can accommodate other actuation components and as a result, the plate member 114 can have a unique geometric shape. In the illustrated embodiment, the plate member 114 has a first tab 146 having a lateral protrusion (not shown) that seats in the opening 144 in the closure actuator. The protrusion can be disposed on a first lateral side of the plate and can be shaped in various ways, but in the illustrated embodiment has a ring-shaped cross-section and an opening 148 extending therethrough. The protrusion can have a width in a lateral direction that is sufficiently large so as to allow the protrusion to be seated in the opening 144 and/or a pin or another type of coupling member (not shown) can extend through the opening 146 in the plate member 114 and through the opening 144 in the closure actuator 106. The plate member 114 can include a second tab 147 (shown in FIG. 5C) having an opening formed therein and the second tab can be received in a clevis member 150 that can be engaged to control ratcheting movement of the closure actuator 106 when the ratcheting mechanism is activated, thus reducing slop and dead actuator control.

The plate member 114 can have a concavely curved surface 152 between the first tab 146 and the second tab 147 or the surface can be substantially straight. In the illustrated embodiment, the curved surface 152 prevents the plate member 114 from contacting other nearby components in the housing 102, such as the clevis member 150. The plate member 114 can also have an extension portion 154 that can have a substantially triangular cross-sectional shape. The extension portion 154 can have a planar proximal-facing surface 154p that can contact a distal facing surface (not shown) of the intermediate shaft sled 118, as will be described in greater detail below. A third tab 156 can be disposed adjacent and proximal to the extension portion 154 which can have another opening (not shown) formed therethrough and can have a curved surface which can provide space for other actuation components such as the locking switch 108 and an elongate rod 158 which extends laterally therefrom and linkage 159. Moving proximally from the third tab 156, one or more surfaces of the plate member 114 can be concavely curved to accommodate the elongate rod of the locking switch 108 and the intermediate shaft sled 118 and can define an arm 160 having a terminal portion 162 sized and shaped to interact with one or more features of the inner shaft sled 116. The terminal portion 162 can include, for example, first and second planar surfaces 161a, 161b and a substantially rectangular shaped tab 163 that is adjacent to the second planar surface 161b. As will be described in greater detail below, when the inner shaft sled 116 is in a retracted position during loading of the end effector, a lateral pin 117 disposed on the inner shaft sled 116 can contact a surface of the rectangular shaped protrusion 163 and can prevent the plate member 114 from pivoting. As shown, the lateral pin 117 can be offset from the longitudinal axis L extending through the elongate shaft 104, which in turn provides a greater mechanical advantage in operation. As a result, the amount of clamping force needed to be applied by a user to close jaws of the end effector is reduced, and the maximum amount of force supplied by jaws to tissue disposed therein can be increased.

The inner shaft sled 116 can interact with various actuation components and can be sized and shaped to facilitate this interaction. In the illustrated embodiment, the inner shaft sled 116 has a substantially rectangular cross-sectional shape. The inner shaft sled 116 can be substantially elongate in a proximal-distal direction and its dimensions can be selected based on the dimensions of the plate member 114 to allow the plate member 114 to interact with the lateral pin 117 when the components are in the ready-to-load position. The inner shaft sled 116 can include first and second wings 165, 167 that can extend laterally from and be flush with an upper surface of the inner shaft sled 116. The first and second wings 165, 167 can each have a planar lateral surface with a substantially rectangular cross-sectional shape but with rounded corners. In certain aspects, the planar surfaces 169, 171 of each of the wings 165, 167 can be seated in first and second tracks (not shown) formed on an inner surface of the housing to stabilize and guide movement of the inner shaft sled 116. A proximal facing surface of the first wing 165 can have a cutout or recess 170 formed therein and configured to allow the rectangular shaped protrusion 163 of the plate member 114 to move therethrough as the plate member 114 pivots relative to the housing. The inner shaft sled 116 can be fixedly coupled to a proximal end (not shown) of the inner shaft 138 or an intermediate component that can engage the inner shaft 138 such that moving the inner shaft sled 116 in a proximal or distal direction can cause a corresponding movement of the inner shaft 138. The inner shaft sled 116 can further include one or more features that can mate with a sliding coupler 176, such as an extension arm 172 having a mating feature 174 formed on a distal end thereof that can be received in and couple to a corresponding mating recess 173 formed in the sliding coupler 176.

The housing can also include the intermediate shaft sled 118, also referred to as an end effector sled because distal advancement of the intermediate shaft 128 can actuate the end effector 30. The intermediate shaft sled 118 can control movement of the intermediate shaft 128 having the arms 128a, 128b by pushing a flange 121 disposed at a proximal end 128p of the intermediate shaft 128 with a pusher 123. The intermediate shaft sled 118 can have a proximal end 118p with a rectangular cuboid shaped cutout or recess 119 that creates space for first and second linkages 120a, 120b which are coupled to the proximal end of the sled 118. The intermediate shaft sled 118 can be shaped in various ways, but in the illustrated embodiment has a substantially rectangular cross-sectional shape with a rounded proximal end. Similar to the inner shaft sled 116, the intermediate shaft sled 118 can also have lateral wings 178a, 178b that can seat in corresponding tracks formed in an inner surface of the housing. The intermediate shaft sled 118 can also include first and second protrusions 180a, 180b extending in a vertical direction configured to mate with extensions 181a, 181b extending laterally from the sliding coupler 176. This can allow the intermediate shaft sled 118 and the sliding coupler 176 to move together as a unit. As a result, when the intermediate shaft sled 118 moves proximally, a shelf 176s (see FIG. 5C) internal to the coupler 176 contacts and pulls the flange 121, and thus the intermediate shaft 128, proximally to retract the intermediate shaft 128. The intermediate shaft sled 118 can include other features such as a recess or cutout 182 formed in the lateral wing 178 that includes a curved bottom-facing surface and a planar distal-facing surface. The recess 182 can be sized an shaped to allow the extension portion of the plate member 114 to move within the recess 182 and the distal-facing surface can also act as a stop to prevent the plate member 114 from pivoting beyond a particular angle.

FIGS. 5A-5C also illustrate a release button 177 extending from an upper surface of the housing 102 and configured to be manually operated by a user to release the intermediate and/or inner shafts 128, 138 from the housing 102. The release button 177 can include a housing 179 having a space 181 for the intermediate and inner shafts 128, 138 and the elongate shaft 104 to extend therethrough. This release button 177 can be selectively depressed by a user to cause a linkage 183 (biased upwards toward the button 177 by a spring 183s disposed between the linkage 183 and an inner surface of the housing 102) to slide toward a lower portion of the housing 102, against the bias. This movement allows the sliding coupler 176 to slide in the same direction and allows the mating feature 174, and thus the inner shaft sled 116, to disconnect from the coupler 176. This movement of the sliding coupler 176 with respect to the intermediate shaft sled 118 frees the intermediate shaft 128 to be selectively removed from the housing 102, while separation of the mating feature 174 and inner shaft sled 116 from the sliding coupler 176 frees the inner shaft 138 to be selectively removed from the housing 102.

The device 100 can include various features and configurations to facilitate cleaning of the components. For example, the housing 102 can be separated into two halves, piece 102a and piece 102b, as shown in FIG. 5C. The internal actuation components of the housing 102 can be restrained and seated in one side, e.g., piece 102a, such that the other side, e.g., piece 102b, can be removed, allowing for easy access for cleaning. In some embodiments, the two pieces 102a, 102b can be coupled together using rare earth magnets and these magnets can be positioned in one side, e.g., piece 102a, to allow for easy attachment and release of the other side, e.g., piece 102b. By way of further non-limiting example, a flush port can be incorporated into the housing 102 and can be used to ensure that the elongate shaft 104, the intermediate shaft 128, and the inner shaft 138 can be cleaned. Additionally, the modularity of the shafts 128, 138, 104 discussed above can facilitate cleaning of the shafts since they can be removed, cleaned, and then replaced.

Figure 6:
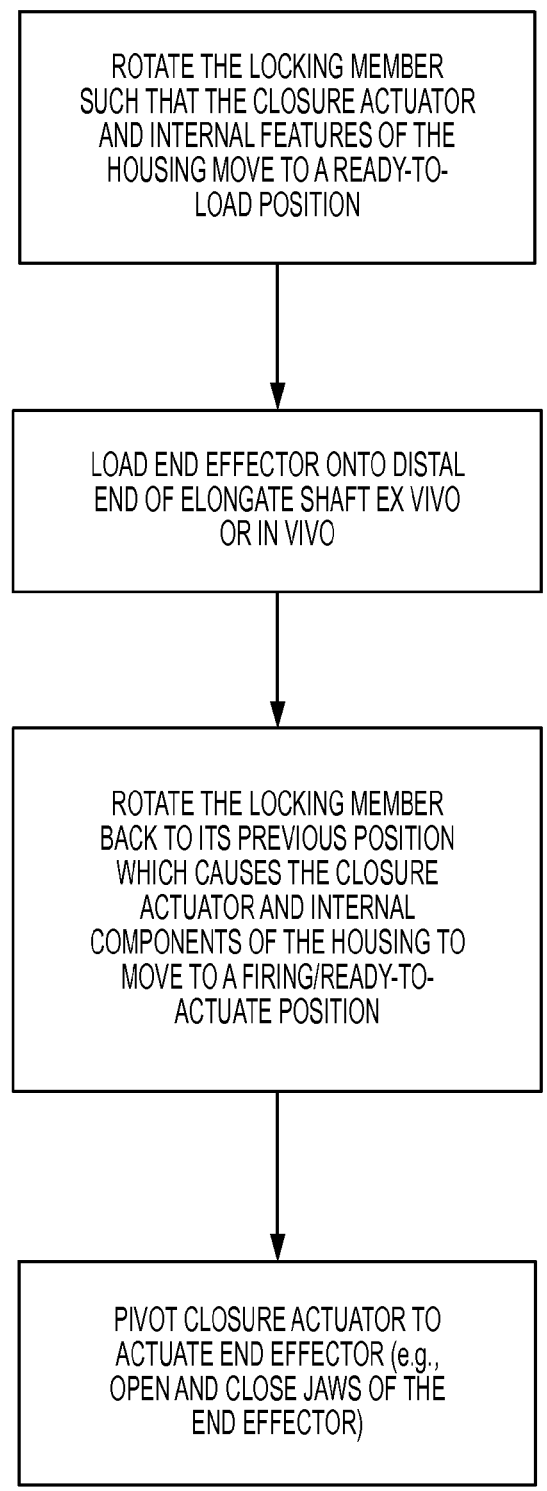
FIG. 6 is a flow chart illustrating an exemplary method of loading an end effector onto the surgical device of FIG. 1A.

FIG. 6 illustrates an exemplary method for engaging and disengaging the locking member 112 of the surgical device 100. The method can include actuating the locking member 112 by rotating it counter clockwise which in turn causes the closure actuator 106 and internal actuation components of the housing move to a ready-to-load position (see also FIG. 7C, described below). More specifically, the closure actuator 106 and the internal actuation components move proximally. An end effector 30 can be loaded onto the distal end 104d of the elongate shaft 104 ex vivo or in vivo. After the end effector 30 is loaded onto the shaft 104, the user can move the locking member 112 in the opposite direction, i.e., rotate the locking member 112 in a clockwise direction. As a result, the closure actuator 106 can move away from the housing 102 and the closure actuator 106 can be freely movable relative to the housing 102 to allow a user to actuate the end effector 30 coupled to the elongate shaft 104. In another embodiment, the locking member, 112 the internal actuation components, and the closure actuator 106 can automatically move to the ready-to-actuate position in response to the end effector 30 being loaded onto the elongate shaft 104.

FIG. 7A illustrates the internal components of the housing 102 in a first, resting position prior to loading an end effector 130. In this position, an outer surface of the locking member 112 extends along a proximal, upper surface of the housing 102. The first and second arm portions 106a, 106b of the closure actuator 106 are angled away from the housing 102. The sliding coupler 176, the inner shaft sled 116, and the intermediate shaft sled 118 are in their distal-most positions with respect to the stationary arm 103 and the housing 102. The first tab 146 of the plate member 114 is seated in the second rounded end 144e of the opening 144 of the closure actuator 106. The rectangular shaped tab 163 of the plate member 114 is positioned in the recess 170 formed in the first wing 165 of the inner shaft sled 116 but does not contact the inner shaft sled 116. The terminal portion of the plate member 114 where the first and second planar surfaces 161a, 161b meet can contact the lateral pin 117 that extends laterally from the inner shaft sled 116. Still further, the extension arm 172 of the inner shaft sled 116 can be received in and mate with the sliding coupler 176.

Figure 7B:
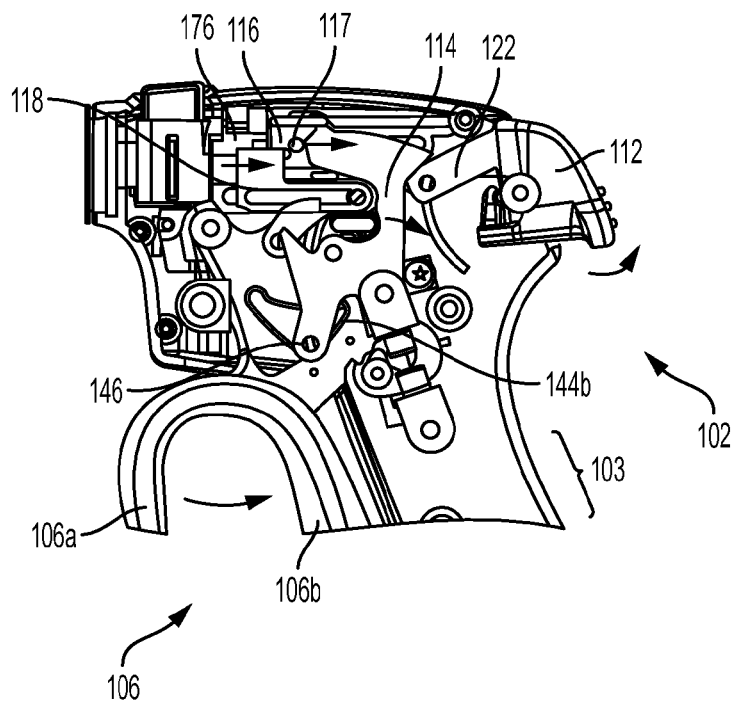
FIG. 7B is a side, semi-transparent view of the housing of FIG. 7A with the locking member and closure actuator being pivoted relative to the housing.

With the components so positioned, a user can apply a pivoting force to the locking member 112 in the counter clockwise, proximal direction as shown in FIG. 7B to begin moving the actuation components to the ready-to-load position. This can be accomplished while a user grasps the stationary arm 103 with his or her palm and uses one or more fingers and/or a thumb from the same hand to pivot the locking member 112. At the same time, earlier, or later, the user can also use one or more fingers to operate the closure actuator 106. The user's palm can be grasping the stationary arm 103 as the locking member 112 is moved by one or more fingers and/or thumb of that same hand, and further, one or more finger(s) and/or thumb from that same hand can be used to operate the closure actuator 106.

Figure 7C:
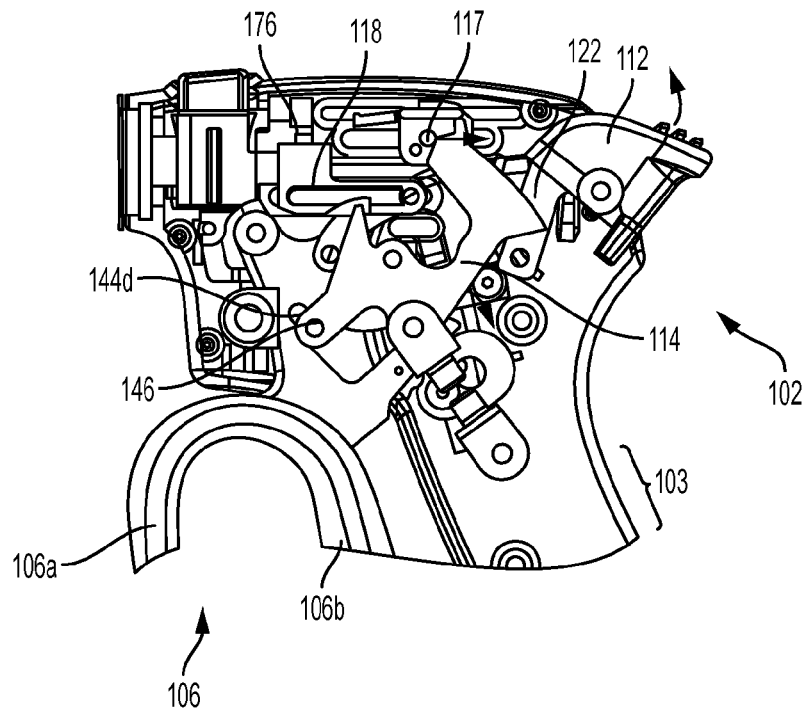
FIG. 7C is a side, semi-transparent view of the housing of FIG. 7B with the locking member and the closure actuator being just before a ready-to-load position in which the device is configured to receive an end effector.

The pivoting of the locking member 112 can cause the closure actuator 106 to pivot toward the housing 102 and the first tab 146 of the plate member 114 can advance distally and along the second planar surface 144b of the opening 144 in the closure actuator 106. This can also apply a proximal force to the linkage 140 that couples the internal arm 122 of the locking member 112 to the inner shaft sled 116. Because the inner shaft sled 116 is coupled to the sliding coupler 176 via the extension arm 172 and the coupler 176 engages the flange 121 disposed at the distal end 138d of the inner shaft 138 with its internal shelf 176s, proximal movement of the inner shaft sled 116 causes the sliding coupler 176 and the intermediate shaft sled 118 coupled thereto to move proximally with respect to the housing 102, as show by the respective arrows. Proximal movement of the inner shaft sled 116 can cause the lateral pin 117 to also move proximally and pivot the plate member 114 in a clockwise direction as shown by the respective arrow. The movement of the components and the pivoting of the plate member 114 are also shown in FIG. 7C illustrating the locking member 112 being pivoted toward and just before it reaches the ready-to-load position, the first tab 146 of the plate member moving toward the first rounded end 144d of the opening 144 in the closure actuator 106.

Figure 7D:
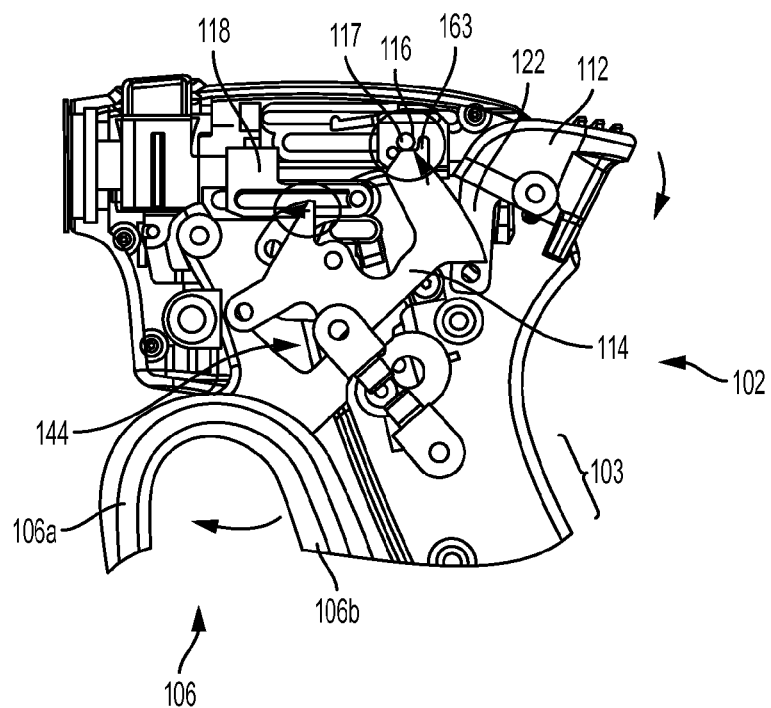
FIG. 7D is a side, semi-transparent view of the housing of FIG. 7C illustrating the closure actuator at the ready-to-load position and ready to subsequently be moved to a ready-to-actuate position in which the device is configured to actuate the end effector.

When the components are in the ready-to-load position of FIG. 7D, the pin 117 of the inner shaft sled 116 rests against a distal-facing surface of the rectangular shaped tab 163 of the plate member 114, preventing the plate member 114 from pivoting distally in a counter clockwise direction. Additionally, the locking member 112 cannot be pivoted further in the counter clockwise direction. The second arm 106b of the closure actuator 106 can be positioned adjacent to the stationary arm 103 or generally spaced at a distance from the stationary arm 103 that is smaller than when the closure actuator 106 is in the first, resting position. In either example, the closure actuator 106 is in a fixed position and a user cannot move the closure actuator 106 relative to the housing 102. As previously mentioned, this can ensure that a user does not try to actuate the closure actuator 106 prior to an end effector being loaded onto the device 100.

Though not shown, at this time an end effector can be loaded onto the device 100 and then the sliding coupler 176, the inner shaft sled 116, the intermediate shaft sled 118, the closure actuator 106, and the locking member 112 can return to the position of FIG. 7A. This can be accomplished by pivoting the locking member 112 in a clockwise direction back to the position of FIG. 7A using the same single hand which can be primarily disposed around the stationary arm 103. This will cause the inner shaft sled 116 and the intermediate shaft sled 118 to slide distally to their distal position and will allow the plate member 114 to pivot in a counter clockwise direction until the actuation components and the closure actuator 106 are in the position of FIG. 7A, as illustrated by the respective arrows in FIG. 7D. Notably, as the intermediate shaft sled 118 advances distally, the plate member 114 is able to rotate to the ready-to-fire position because its movement is no longer restricted by the pin 117. This likewise frees the closure actuator 106 to move to the ready-to-fire position and be operated by the user as desired.

A method for performing a surgical procedure can include passing the elongate shaft 104 of the surgical instrument 100 through a first incision 300 as shown in FIG. 8. The first incision 300 can be a percutaneous incision formed at least partially by a puncture formed with the distal obturator tip of the inner shaft (not shown) or the incision can be formed using a separate instrument. As the elongate shaft 104 passes through the incision 300 in a tissue wall 302, the device can be in the first, resting position of FIG. 7A and the distal tip of the inner shaft and the arms of the intermediate shaft can be in the distal position beyond the distal end of the elongate shaft 104 or the device can be in the ready-to-load position of FIG. 7D. An end effector can be selected from a plurality of end effectors provided in a kit (though the description below refers to the end effector 130, any end effector can be used) and the loading process can begin as in FIG. 8A. The end effector 130 can be loaded ex vivo into the distal end of the loader 200. In this example, the end effector 130 has tissue grasping jaws, but as previously mentioned a variety of other end effectors could also be used. The distal end of the loader 200 with the end effector 130 loaded therein can be passed through a second incision 400 formed in a tissue wall 402 as shown. The second incision 400 can also be percutaneous incision spaced from the first incision 300. If pneumoperitoneum is desired, the incisions 300, 400 can have instrument seals such as by positioning a trocar in each incision and inserting the surgical instrument 100 or loader 200 through the trocar. In other embodiments, trocars need not be used and instead the resilience of the tissue can form a seal around the shaft 104, 202 of the instrument 100, 200 without the aid of a separate trocar or sealing device.

The tissue wall anatomies will vary based on the surgical procedure, but some non-limiting examples include percutaneous incisions extending into the abdomen, thorax, or pelvis. The incisions 300, 400 can be formed with a cutting or puncturing instrument and will typically be spaced apart from one another. The tissue walls 302, 402 can be the same or different anatomies. For example, tissue walls 302, 402 can both be the abdominal wall. In another example, the tissue wall could be an organ (e.g., stomach, colon, esophagus, etc.) accessed through a natural orifice, while the incision in tissue wall can be percutaneous. In yet another example, the first incision 300 can provide access to the abdomen, while the second incision 400 can provide access to the pelvis. The surgical end effector 130 can be selectively attachable in vivo and detachable in vivo to the attachment mechanism/loading zone located at the distal end of the elongate shaft 104 of the instrument 100. For in vivo attachment, the loader 200 can hold the end effector 130 during attachment to and detachment from the surgical instrument 100. The distal portion 204 of the loader 200 is typically introduced and removed through an incision in-line with the shaft 202 and then articulated about the joint 205 in vivo to align the end effector 130 with the shaft 104 of the surgical instrument 100. In another embodiment, the end effector 130 can be loaded ex vivo onto the distal end 104d of the shaft 104 and then introduced into the surgical field through the first incision 300.

Figure 8A:
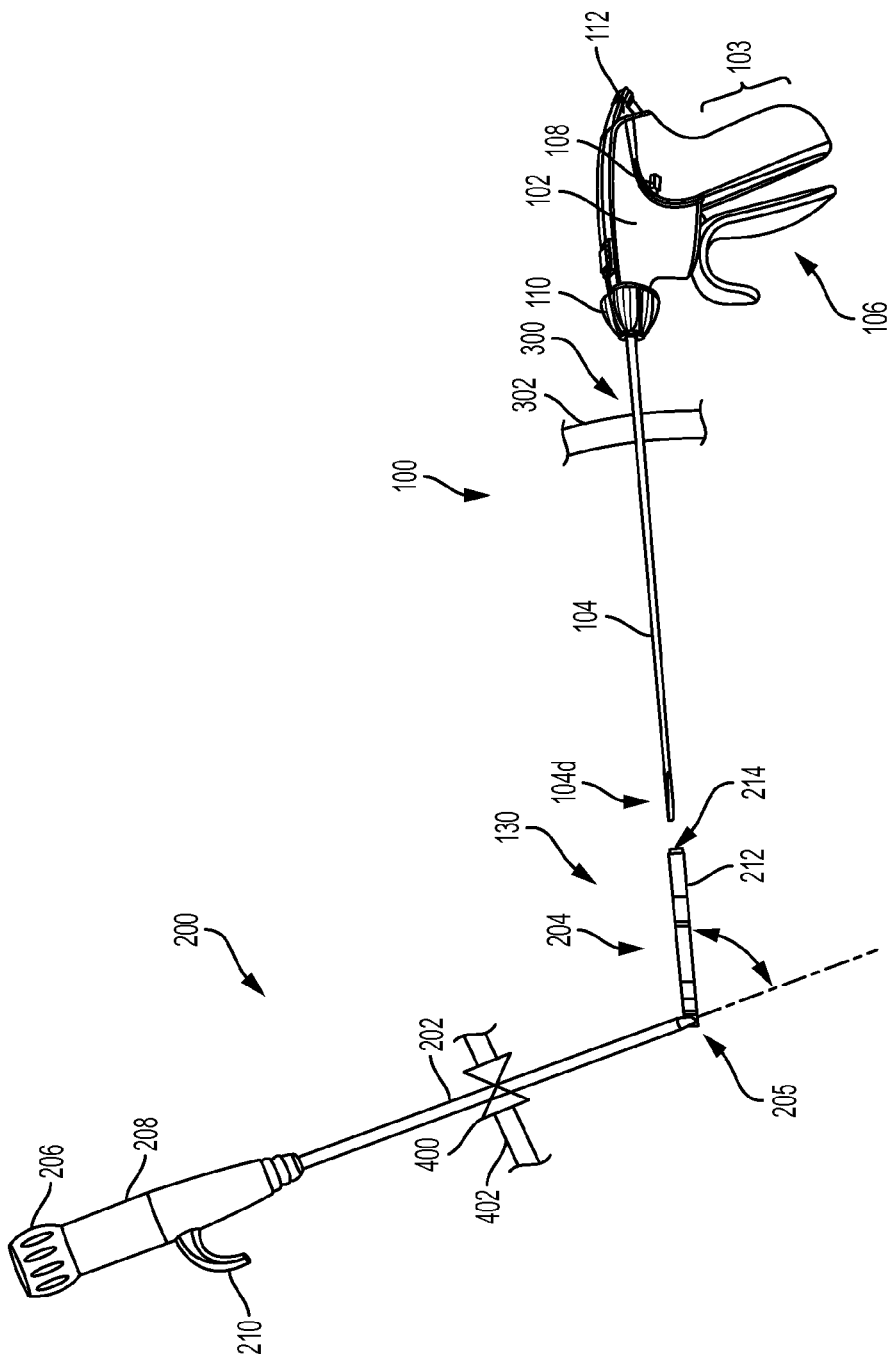
FIG. 8A is a perspective view of the surgical device of FIG. 1A and the loading device of FIG. 4 prior to loading an end effector onto the surgical device.
Figure 8B:
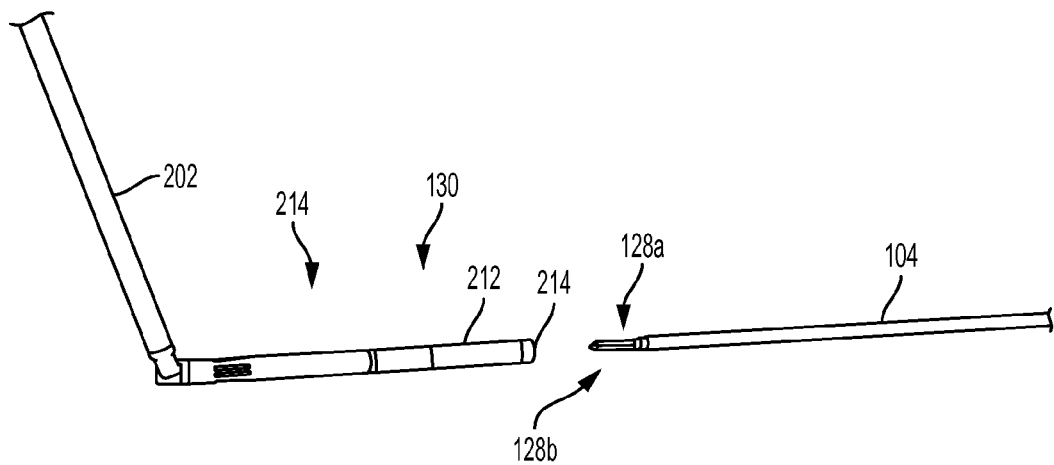
FIG. 8B is a perspective view of the mating feature of the elongate shaft of the surgical device of FIG. 8A being positioned adjacent to and axially aligned with the loading device of FIG. 8A.
Figure 8C:
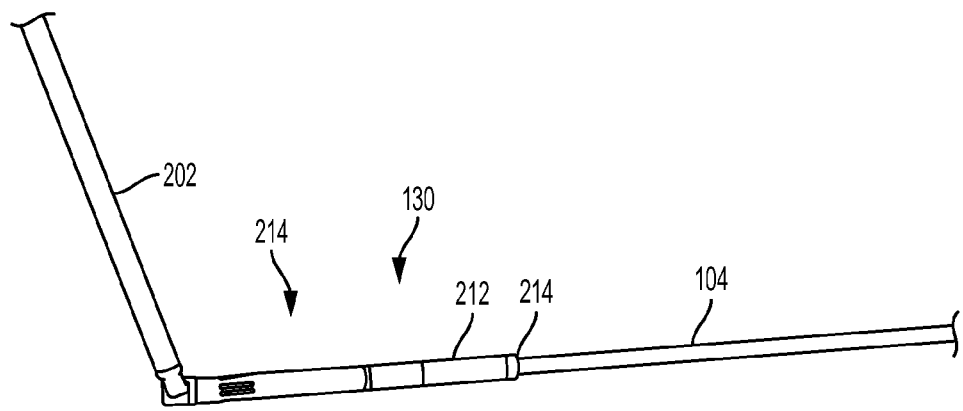
FIG. 8C is a perspective view of the mating feature of the elongate shaft coupling to an end effector on the loading device of FIG. 8B.

The distal portion 204 of the loader 200 can be articulated relative to the shaft 202 of the loader 200 as desired so as to align the proximal end of the end effector 130 and the attachment mechanisms of the surgical instrument 100 to form the loading zone, as shown in FIG. 8B. The locking member 112 can be pivoted counterclockwise and this can cause the sliding coupler 176, the inner shaft sled 116, and the intermediate shaft sled 118 to slide proximally within the housing 102. The device 100 can be advanced distally toward a proximal end of the end effector 130 until the distal end of the shaft 104 is disposed in the distal portion 204 of the loader 200 as shown in FIG. 8C. The arms 128a, 128b can deflect medially so as to create a smaller size profile that can fit inside of the end effector's tube 212. After the end effector 130 is onto the shaft 104 and engages with the ridge of the arms, a user can pivot the locking member 112 back to its first, resting position to cause the end effector 130 to lock onto the shaft 104 by the arms and the distal tip moving distally. Alternatively, loading the end effector 130 onto the shaft 104 can automatically cause the sliding coupler 176, the inner shaft sled 116, and the intermediate shaft sled 118 to move distally and the distal tip of the inner shaft and the arms of the intermediate shaft 118 can engage with the end effector 130. In both embodiments, the closure actuator 106 will have returned to its first position angled away from the housing 102. This position is also referred to as a ready-to-actuate position because the end effector 130 is now coupled to the device 100.

Figure 8D:
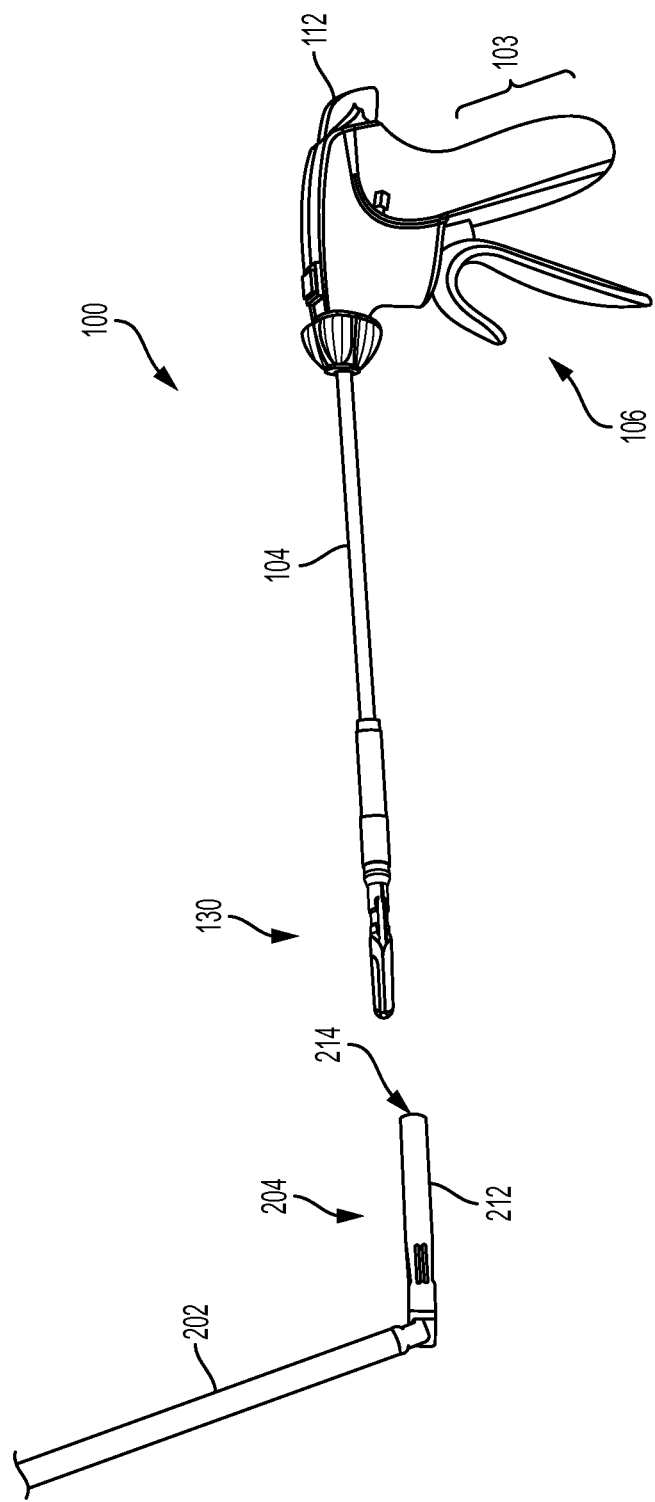
FIG. 8D is a perspective view of the end effector of FIG. 3A coupled to the surgical device of FIG. 8C.

With the end effector 130 attached to the device 100, a force can be applied in a proximal direction to the housing 102 of the device 100 to withdraw the end effector 130 from the loader 200 as shown in FIG. 8D. Tissue can be then manipulated using the device 100 by actuating the closure actuator 106 of the housing 102 (e.g., moving the closure actuator toward or away from the housing 102) to move the intermediate shaft sled 118 to operate the end effector 130, e.g., open and close the pivot jaws. With the end effector 130 properly loaded onto the device 100, the ratcheting features of the closure actuator 106 can be engaged if desired by depressing or otherwise activating the locking switch 108 disposed on the housing 102 prior to or after the closure actuator 106 is pivoted toward the housing 102. Activating the locking switch 108 can hold the closure actuator 106 in a fixed position even when a user stops applying a force to hold the closure actuator 106 and can still allow a user to incrementally advance the closure actuator 106 toward the housing 102.

After completing the surgical procedure, the end effector 130 can be detached from the shaft ex vivo or in vivo. If the loader 200 was previously removed, the loader can be reintroduced 200 through the second incision into the surgical field to allow for in vivo detachment of the end effector 130. The distal end of the end effector 130 can be inserted and seated in the distal end of the loader 200, and the inner shaft can be moved proximally to its unlocked position by pivoting the locking member 112 to the ready-to-load position. The arms can also move proximally by moving the locking member 112 to the ready-to-load position. The end effector 130 can be held in the loader 200 by the engagement feature (not shown) and the distal end of the shaft 104 can then be withdrawn leaving the end effector 130 in the loader 200 and thereby detaching the end effector 130 from the instrument 100. The loader 200 having the end effector 130 disposed therein can be removed from the surgical field. A different end effector 130 can then be inserted into the loader 200 and then attached to the surgical instrument 100 using the steps described above or the surgical instrument 100 can be withdrawn from the surgical field.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical device, comprising:
a housing;
a closure actuator coupled to the housing and configured to pivot with respect to the housing;
an elongate shaft extending distally from the housing, the elongate shaft having a loading zone located at a distal end of the elongate shaft, the loading zone being configured to receive an end effector;
an inner shaft disposed within an inner lumen of the elongate shaft, the inner shaft having a proximal end coupled to one or more actuation components disposed within the housing, the inner shaft being configured to translate relative to the elongate shaft along a longitudinal axis thereof, and the inner shaft being configured to lock the end effector to the distal end of the elongate shaft at the loading zone when a distal end of the inner shaft is disposed within a portion of the inner lumen contained within the loading zone; and
a locking member operably coupled to the one or more actuation components, the one or more actuation components also being coupled to the closure actuator such that movement of the locking member effects movement of the closure actuator;
wherein the locking member is configured to move to a load position in which the closure actuator is held at a fixed location with respect to the housing such that the end effector can be loaded onto the distal end of the elongate shaft at the loading zone;

wherein when the locking member is in the load position, the distal end of the inner shaft is located proximal of the loading zone; and wherein the one or more actuation components comprises a plate pivotally coupled to the closure actuator and configured to be slidably coupled to the inner shaft.

2. The device of claim 1, wherein the one or more actuation components further comprises:

a sled coupled to the proximal end of the inner shaft and configured to slide along a path within the housing, the sled engaging the plate when the sled is positioned on a proximal portion of the path; and a linkage having a first end coupled to the locking member and a second end coupled to the sled.

3. The device of claim 1, wherein the closure actuator comprises an opening formed in a portion thereof, with at least a portion of the opening being disposed within the housing, and a cam surface that is configured to move the closure actuator towards the fixed location in response to the locking member moving to the load position.

4. The device of claim 1, wherein the locking member has a use position at which the closure actuator is located further from the housing than when the locking member is in the load position.

5. The device of claim 1, further comprising an intermediate shaft disposed between the elongate shaft and the inner shaft, the intermediate shaft having an advanced position in which a portion of the intermediate shaft that extends distally beyond the distal end of the elongate shaft is part of the loading zone.

6. A surgical device, comprising:

a housing;

a closure actuator coupled to the housing at a lower portion of the housing, the closure actuator being configured to pivot with respect to the housing;

an elongate shaft extending distally from a distal, upper portion of the housing, the elongate shaft having a distal end configured to receive an end effector;

an inner shaft disposed within an inner lumen of the elongate shaft and being configured to translate relative to the elongate shaft along a longitudinal axis thereof, the inner shaft further being configured to lock the end effector to the distal end of the elongate shaft when a distal end of the inner shaft is disposed within a portion of the inner lumen that has the end effector disposed therearound;

a locking member extending from a proximal, upper portion of the housing, the locking member being configured to move between a loading position at which the end effector can be loaded onto the distal end of the elongate shaft, and a firing position at which the closure actuator can be actuated to control the end effector loaded onto the distal end of the elongate shaft; and a plate disposed within the housing and pivotally coupled to the closure actuator and configured to be slidably coupled to the inner shaft;

wherein, when in the loading position, the locking member locks the closure actuator in a fixed position such that actuation of the closure actuator is prevented;

wherein when the locking member is in the loading position, the distal end of the inner shaft is located proximal of the portion of the inner lumen that has the end effector disposed therearound, and when the locking member is in the firing position, the distal end of the inner shaft is located within the portion of the inner lumen that has the end effector disposed therearound.

7. The device of claim 6, wherein the locking member is configured to pivot with respect to the housing between the loading position and the firing position.

8. The device of claim 6, wherein the housing further comprises a handle portion configured to be gripped by a hand of an operator, the locking member being configured to be controlled by one or more fingers or thumb of the hand of the operator while the hand remains gripping the handle portion.

9. The device of claim 6, further comprising an intermediate shaft disposed between the elongate shaft and the inner shaft, the intermediate shaft having an advanced position in which a portion of the intermediate shaft that extends distally beyond the distal end of the elongate shaft is configured to receive the end effector.

10. The device of claim 6, further comprising:

a sled configured to travel along a path within the housing and coupled to a proximal end of the inner shaft, the sled engaging the plate when the sled travels along a portion of the path; and a linkage disposed within the housing, the linkage having a first end coupled to the locking member and a second end coupled to the sled.

11. The device of claim 10, further comprising a pin disposed on the sled and configured to prevent the plate and the closure actuator from moving when the closure actuator is in the loading position.

12. A surgical device, comprising:

a housing;

a closure actuator coupled to the housing and configured to pivot with respect to the housing;

an elongate shaft extending distally from the housing, the elongate shaft having a loading zone located at a distal end of the elongate shaft, the loading zone being configured to receive an end effector; and a locking member operably coupled to one or more actuation components disposed within the housing and configured to pivot with respect to the housing, the one or more actuation components also being coupled to the closure actuator such that pivotal movement of the locking member causes pivotal movement of the closure actuator, wherein the locking member is configured to pivot to a load position in which the closure actuator is held at a fixed location with respect to the housing such that the end effector can be loaded onto the distal end of the elongate shaft at the loading zone.

13. The device of claim 12, wherein the one or more actuation components comprises a plate pivotally coupled to the closure actuator.

* * * * *